US007728109B2

(12) United States Patent
Kikly

(10) Patent No.: US 7,728,109 B2
(45) Date of Patent: *Jun. 1, 2010

(54) ANTAGONISTIC ANTI-HTNFSF13B HUMAN ANTIBODIES

(75) Inventor: Kristine Kay Kikly, Fortville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 96 days.

This patent is subject to a terminal disclaimer.

(21) Appl. No.: 11/952,363

(22) Filed: Dec. 7, 2007

(65) Prior Publication Data

US 2008/0175841 A1 Jul. 24, 2008

Related U.S. Application Data

(63) Continuation of application No. 10/484,790, filed on Jan. 22, 2004, now Pat. No. 7,317,089.

(51) Int. Cl.
C07K 16/24 (2006.01)
(52) U.S. Cl. .................. 530/387.1; 530/351; 530/387.3; 530/388.15; 530/388.23
(58) Field of Classification Search ............ 530/388.15, 530/388.23, 387.3, 387.1, 351
See application file for complete search history.

(56) References Cited

U.S. PATENT DOCUMENTS

| | | | |
|---|---|---|---|
| 6,096,878 | A | 8/2000 | Hongo et al. |
| 6,297,367 | B1 | 10/2001 | Tribouley |
| 6,403,770 | B1 | 6/2002 | Yu et al. |

FOREIGN PATENT DOCUMENTS

| | | |
|---|---|---|
| EP | 939804 | 5/1998 |
| EP | 1157110 | 8/2000 |
| WO | WO 97/13852 | 4/1997 |
| WO | WO 98/18921 | 5/1998 |
| WO | WO 98/27114 | 6/1998 |
| WO | WO 99/12964 | 3/1999 |
| WO | WO 00/32635 | 6/2000 |
| WO | WO 00/43032 | 7/2000 |
| WO | WO 00/50597 | 8/2000 |
| WO | WO 02/002641 | 10/2002 |

OTHER PUBLICATIONS

Harindranath, N. et al., "Complete sequence of the genes encoding $V_H$ and $V_L$ regions of low-and high- affinity monoclonal IgM and IgA1 rheumatoid factors produced by CD5+ B cells from a rheumatoid arthritis patient." Int. Immunology, vol. 3, pp. 865-875, 1991.
Allikmets, R., et al. "Characterization of the Human ABC Superfamily: Isolation and Mapping of 21 New Genes Using the Expressed Sequence Tags Database." Human Molecular Genetics, vol. 5, No. 10, 1996, pp. 1649-1655.
Altschul, S., et al. "Basic Local Alignment Search Tool." J. Mol. Biology, vol. 215, 1990, pp. 403-410.

Armitage, Richard J. "Tumor Necrosis Factor Receptor Superfamily Members and their Ligands." Current Opinion in Immunology, No. 6, 1994, pp. 407-413.
Beutler, B. et al. "Unraveling Function in the TNF Ligand and Receptor Families." Science, vol. 264, Apr. 1994, pp. 667-668.
Boguski, M. "The Turning Point in Genome Research." TIBS 20, Aug. 1995.
Cheema, G., et al. "Elevated Serum B Lymphocyte Stimulator Levels in Patients With Systemic Immune-Based Rheumatic Diseases." Arthritis & Rheumatism, vol. 44, No. 6, Jun. 2001, pp. 1313-1319.
Do, R., et al. "Attenuation of Apoptosis Underlies B Lymphocyte Stimulator Enhancement of Humoral Immune Response." J. Exp. Med., vol. 192, No. 7, Oct. 2, 2000, pp. 953-964.
Gray, P., et al. "Cloning and Expression of cDNA for Human Lymphotoxin, a Lymphokine with Tumour Necrosis Activity." Nature, vol. 312, Dec. 1984, pp. 721-724.
Groom, J., et al. "Association of BAFF/BLyS OverExpression and Altered B Cell Differentiation with Sjogren's Syndrome." The Journal of Clinical Investigation, vol. 109, No. 1, Jan. 2002, pp. 59-68.
Gross, J., et al. "TACI and BCMA are Receptors for a TNF Homologue Implicated in B-cell Autoimmune Disease." Nature, vol. 404, Apr. 2000, pp. 995-998.
Gruss, H. J. "Molecular, Structural, and Biological characteristics of the Tumor Necrosis Factor Ligand Superfamily." Clin. Lab Res, vol. 26, 1996, 99.143-159.
Gruss, H. and Dower, S. "Tumor Necrosis Factor Ligand Superfamily: Involvement in the Pathology of Malignant Lymphomas." Blood, vol. 85, No. 12, Jun. 1995, pp. 3378-3404.
Khare, S., et al. "Severe B Cell Hyperplasia and Autoimmunce Disease in TALL-1 Transgenic Mice." PNAS, vol. 97, No. 7, Mar. 2000, pp. 3370-3375.
MacKay, F. et al. "Mice Transgenic for BAFF Develop Lymphocytic Disorders Along with Autoimmune Manifestations." J. Exp. Med, vol. 190, No. 11, Dec. 6, 1999, pp. 1697-1710.
Moore, P., et al. "BLyS: Member of the Tumor Necrosis Factor Family and B Lymphocyte Stimulator." Science, vol. 285, Jul. 1999, pp. 260-263.

(Continued)

*Primary Examiner*—Stephen L Rawlings
(74) *Attorney, Agent, or Firm*—Sanjay M. Jivraj; Gregory A. Cox

(57) ABSTRACT

Human monoclonal antibodies that specifically bind to TNFSF13b polypeptides are disclosed. These antibodies have high affinity for hTNFSF13b (e.g., $K_D = 10^{-8}$ M or less), a slow off rate for TNFSF13b dissociation (e.g., $K_{off} = 10^{-3}$ sec$^{-1}$ or less) and neutralize TNFSF13b activity in vitro and in vivo. The antibodies of the invention are useful in one embodiment for inhibiting TNFSF13b activity in a human subject suffering from a disorder in which hTNFSF13b activity is detrimental. Nucleic acids encoding the antibodies of the present invention, as well as, vectors and host cells for expressing them are also encompassed by the invention.

3 Claims, 2 Drawing Sheets

OTHER PUBLICATIONS

Figure 1:
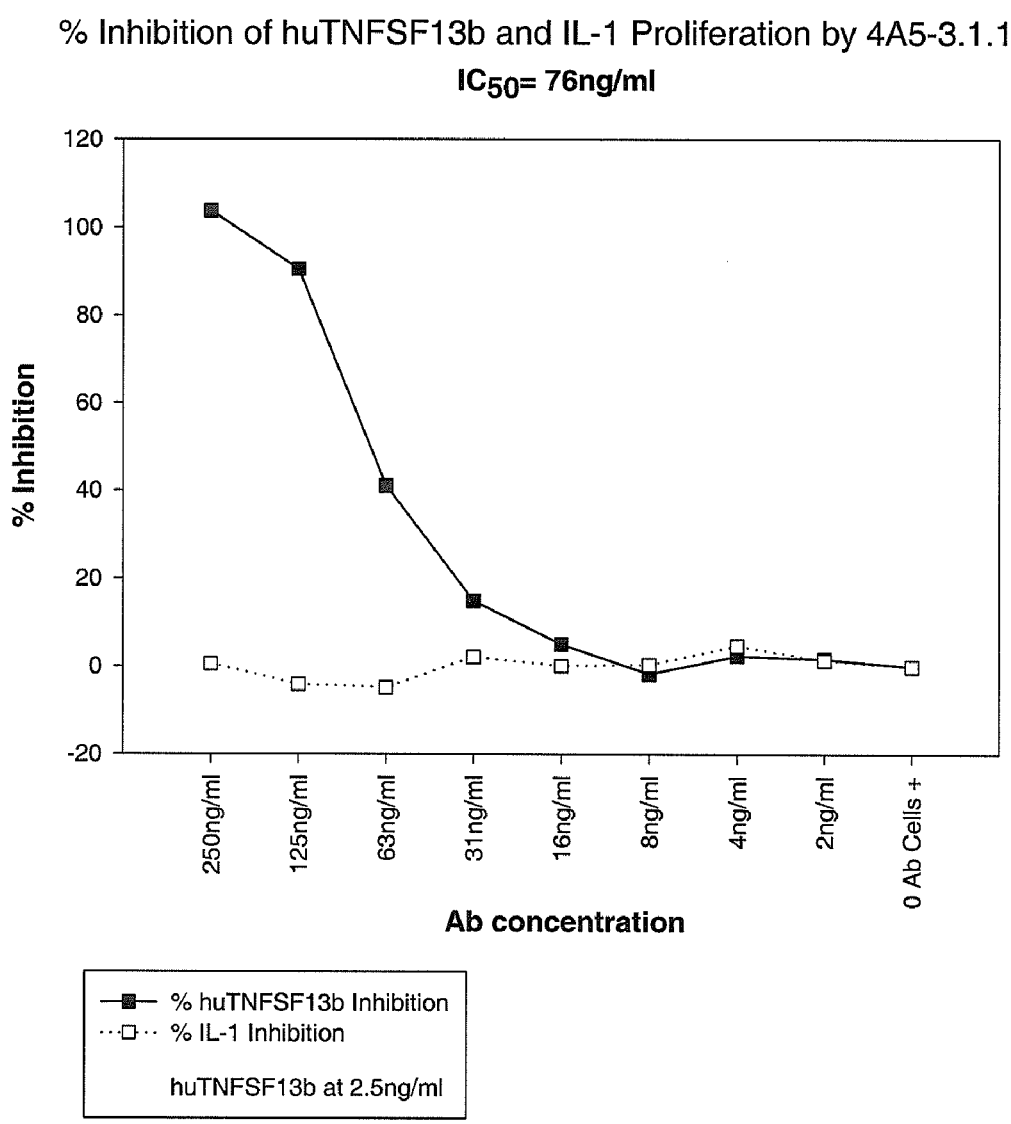

Mukhopadhyay, A., et al. "Identification and Characterization of a Novel Cytokine, THANK, a TNF Homologue That Activates Apoptosis, Nuclear Factor-κB, and c-Jun $NH_2$-Terminal Kinase." The Journal of Biological Chemistry, vol. 274, No. 23, Jun. 1999, pp. 15978-15981.

Pennica, D., et al. "Human Tumour Necrosis Factor: Precursor Structure, Expression and Homology to Lymphotoxin." Nature, vol. 312, Dec. 1984, pp. 724-729.

Pitti, R. et al. "Induction of Apoptosis by Apo-2 Ligand, a New Member of the Tumor Necrosis Factor Cytokine Family." The Journal of Biological Chemistry, vol. 271, No. 22, May 1996, pp. 12687-12690.

Schneider, P., et al. "BAFF, a Novel Ligand of the Tumor Necrosis Factor Family, Stimulates B Cell Growth." J. Exp. Med., vol. 189, No. 11, Jun. 1999, pp. 1747-1756.

Shu, H, et al. "TALL-1 is a Novel Member of the TNF Family that is Down-Regulated by Mitogens." Journal of Leukocyte Biology, vol. 65, May 1999, pp. 680-683.

Tribouley, C., et al. "Characterization of a New Member of the TNF Family Expressed on Antigen Presenting Cells." Biol. Chem., vol. 380, Dec. 1999, pp. 1443-1447.

Vaux, D. "The Buzz About BAFF." Journal of Clinical Investigation., vol. 109, No. 1, Jan. 2002, pp. 17-18.

Wiley, S., et al. "Identification and Characterization of a New Member of the TNF Family that Induces Apoptosis." Immunity, vol. 3, Dec. 1995, pp. 673-682.

Wu, K., et al. "Characterization of a Novel Member of the Macrophage Mannose Receptor Type C Lectin Family." The Journal of Biological Chemistry, vol. 271, No. 35, Aug. 1996, pp. 21323-21330.

Zhang, J., et al. "Cutting Edge: A Role for B Lymphocyte Stimulator in Systemic Lupus Erythematosus." The Journal of Immunology, vol. 166, 2001, pp. 6-10.

GenBank Accession No. AA682496.
GenBank Accession No. AA166695.
GenBank Accession No. D79690.
GenBank Accession No. R16882.
GenBank Accession No. T87299.
GenBank Accession No. G30081.

ANTAGONISTIC ANTI-HTNFSF13B HUMAN ANTIBODIES

This application is a Continuation Application of U.S. Ser. No. 10/484,790, filed 22 Jan. 2004, now U.S. Pat. No. 7,317, 089, which claims the priority of U.S. provisional application No. 60/312,808 filed 16 Aug. 2001.

The TNF family ligands are known to be among the most pleiotropic cytokines, inducing a large number of cellular responses, including proliferation, cytotoxicity, anti-viral activity, immunoregulatory activities, and the transcriptional regulation of several genes. The TNF family of cytokines and receptors has undergone a large expansion in the last few years with the advent of massive EST sequencing. TNFSF13b is the official name adopted by the TNF Congress for BLyS, TALL-1, BAFF, THANK, neutrokine-α, and zTNF (for review see Locksley et al. Cell 2001 104:487). Human TNFSF13b (hTNFSF13b) is a 285-amino acid type II membrane-bound protein that possesses a N-terminal cleavage site that allows for the existence of both soluble and membrane bound proteins. Functionally, TNFSF13b appears to regulate B cell and some T cell immune responses.

Studies of septic shock syndrome and other disorders arising from overproduction of inflammatory cytokines have shown that an afflicted host will often counter high cytokine levels by releasing soluble cytokine receptors or by synthesizing high-affinity anti-cytokine antibodies. Methods of treatment that mimic such natural responses are considered as viable therapeutic approaches for alleviating cytokine-mediated disease. Thus, there is a well-recognized need for human antibodies that bind cytokines, such as TNFSF13b, that are involved in the regulation of cellular immune processes with high affinity and that have the capacity to antagonize the activity of the targeted cytokine in vitro and in vivo. Although international patent application WO00/50597 non-descriptively discloses antibodies directed at TNFSF13b, that application does not specifically describe the structural or functional characteristics of such antibodies.

The present invention provides anti-hTNFSF13b human antibodies, or antigen-binding portions thereof. The antibodies of the invention are characterized by high affinity binding to TNFSF13b polypeptides, slow dissociation kinetics, and the capacity to antagonize at least one in vitro and/or in vivo activity associated with TNFSF13b polypeptides.

The present invention also provides anti-hTNFSF13b human antibodies comprising a polypeptide selected from the group consisting of a polypeptide as shown in SEQ ID NO: 2, a polypeptide as shown in SEQ ID NO: 4, a polypeptide as shown in SEQ ID NO: 6, a polypeptide as shown in SEQ ID NO: 8, a polypeptide as shown in SEQ ID NO: 10, a polypeptide as shown in SEQ ID NO: 12, a polypeptide as shown in SEQ ID NO: 14, and a polypeptide as shown in SEQ ID NO: 16.

In another embodiment, the invention provides an isolated anti-hTNFSF13b human antibody which binds to a hTNFSF13b polypeptide and dissociates from the hTNFSF13b polypeptide with a $K_{off}$ rate constant of $1 \times 10^{-4}$ s$^{-1}$ or less, as determined by surface plasmon resonance, or which inhibits TNFSF13b induced proliferation in an in vitro neutralization assay with an $IC_{50}$ of $1 \times 10^{-8}$ M or less.

In an preferred embodiment, the invention provides an isolated anti-hTNFSF13b human antibody that has the following characteristics:

a) inhibits TNFSF13b induced proliferation in an in vitro neutralization assay with an $IC_{50}$ of $1 \times 10^{-8}$ M or less;

b) has a heavy chain CDR3 comprising the amino acid sequence of SEQ ID NO: 16; and c) has a light chain CDR3 comprising the amino acid sequence of SEQ ID NO:8.

The invention also provides methods of treating or preventing acute or chronic diseases or conditions associated with B cell and some T cell activity including, but not limited to, autoimmune disorders, such as systemic lupus erythematosus, rheumatoid arthritis, and/or neoplasia comprising the administration of an anti-hTNFSF13b human antibody of the present invention.

In another embodiment, the present invention provides sequences that encode the novel anti-hTNFSF13b human antibodies, vectors comprising the polynucleotide sequences encoding anti-hTNFSF13b human antibodies, host cells transformed with vectors incorporating polynucleotides that encode the anti-hTNFSF13b human antibodies, formulations comprising anti-hTNFSF13b human antibodies and methods of making and using the same.

In another embodiment, the present invention provides the epitope of the antigen to which the novel anti-hTNFSF13b human antibodies bind. Thus, the invention also provides a use of an antibody that binds the epitope of the present invention thereby neutralizing the TNFSF13b activity for the treatment or prevention of acute or chronic diseases or conditions associated with B cell and some T cell activity including, but not limited to, autoimmune disorders, such as systemic lupus erythematosus, rheumatoid arthritis, and/or neoplasia.

The invention also encompasses an article of manufacture comprising a packaging material and an antibody contained within said packaging material, wherein the antibody neutralizes TNFSF13b activity for treatment or prevention of a human subject suffering from a disorder in which TNFSF13b activity is detrimental, and wherein the packaging material comprises a package insert which indicates that the antibody neutralizes by binding an epitope of TNFSF13b, wherein the epitope comprises lysine at position 71, threonine at position 72, tyrosine at position 73, and glutamic acid at position 105; and a package insert that provides for administration of the dosage form that results in neutralizing TNFSF13b activity.

FIG. 1. Graph illustrating the inhibition of hTNFSF13b and IL-1 induced proliferation of T1165.17 cells by human antibody 4A5-3.1.1-B4.

Figure 2:
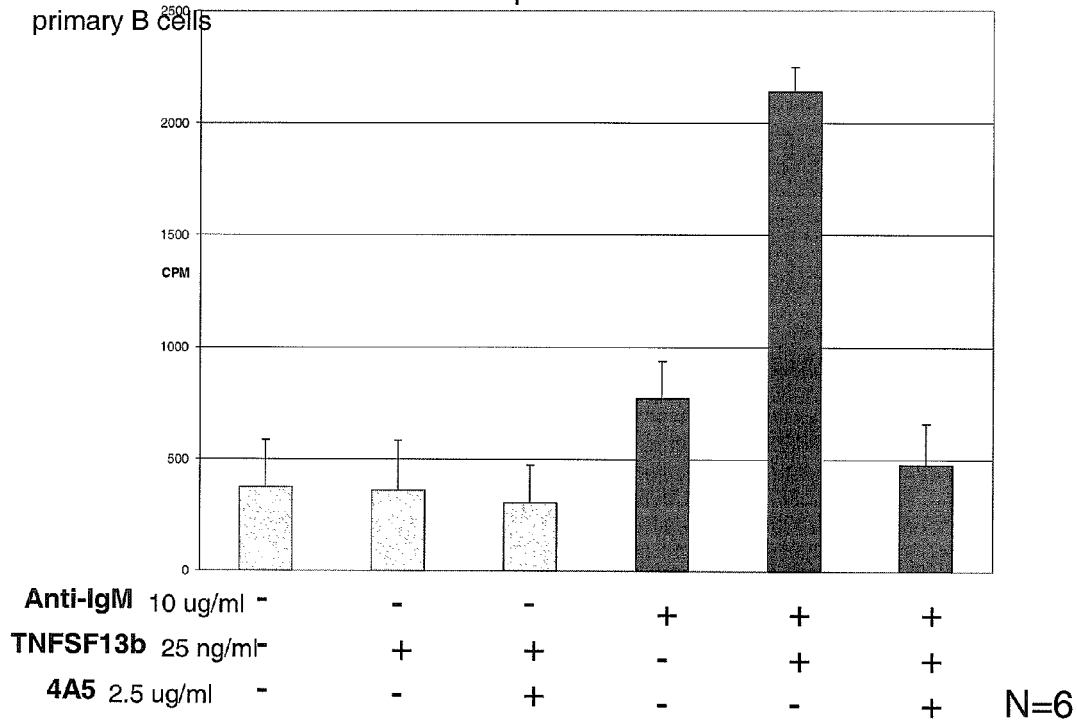

FIG. 2. Graph illustrating the neutralization of hTNFSF13b induced proliferation by human antibody 4A5-3.1.1-B4 in primary human B cells stimulated with anti-IgM.

In order that the present invention may be more readily understood, certain terms are first defined.

An antibody is an immunoglobulin molecule comprised of four polypeptide chains, two heavy (H) chains (about 50-70 kDa) and two light (L) chains (about 25 kDa) inter-connected by disulfide bonds. Light chains are classified as kappa and lambda. Heavy chains are classified as gamma, mu, alpha, delta, or epsilon, and define the antibody's isotype as IgG, IgM, IgA, IgD, and IgE, respectively. Each heavy chain is comprised of a heavy chain variable region (abbreviated herein as HCVR) and a heavy chain constant region. The heavy chain constant region is comprised of three domains, CH1, CH2, and CH3 for IgG, IgD and IgA, and 4 domains, CH1, CH2, CH3, CH4 for IgM and IgE. Each light chain is comprised of a light chain variable region (abbreviated herein as LCVR) and a light chain constant region. The light chain constant region is comprised of one domain, CL. The HCVR and LCVR regions can be further subdivided into regions of hypervariability, termed complementarity determining regions (CDRs), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, FR4. The assignment of amino acids to each domain is in accordance with well known conventions. [Kabat, et al, *Sequences of proteins of Immunological Interest, Fifth Edition*, U.S. Department of Health and Human Services, NIH Publication No. 91-3242 (1991); Chothia, et al., *J. Mol. Biol.* 196:901-917 (1987); Chothia, et al., *Nature* 342:878-883 (1989)]. The functional characteristics of the antibody to bind a particular antigen are determined by the CDRs.

In the present disclosure the term "antibody" is intended to refer to a monoclonal antibody per se. A monoclonal antibody can be a human antibody, chimeric antibody, humanized antibody, Fab fragment, Fab' fragment, F(ab')2, or single chain FV fragment. Preferably the term "antibody" refers to human antibody.

The term "human antibody" includes antibodies having variable and constant regions corresponding to human germ-line immunoglobulin sequences. Human antibodies have several advantages over non-human and chimeric antibodies for use in human therapy. For example, the effector portion of a human antibody may interact better with the other parts of the human immune system (e.g., destroy the target cells more efficiently by complement-dependent cytotoxicity (CDC) or antibody-dependent cellular cytotoxicity (ADCC)). Another advantage is that the human immune system should not recognize the human antibody as foreign, and, therefore the antibody response against such an injected antibody should be less than against a totally foreign non-human antibody or a partially foreign chimeric antibody. In addition, injected non-human antibodies have been reported to have a half-life in the human circulation much shorter than the half-life of human antibodies. Injected human antibodies will have a half-life essentially identical to naturally occurring human antibodies, allowing smaller and less frequent doses to be given.

The term "hTNFSF13b" refers to the human form of a member of the tumor necrosis factor family of ligands described in international patent applications WO98/18921 and WO00/50597 (referred to therein as neutrokine-α). The term "TNFSF13b" is intended to encompass hTNFSF13b as well as homologs of hTNFSF13b derived from other species. The terms "hTNFSF13b" and "TNFSF13b" are intended to include forms thereof, which can be prepared by standard recombinant expression methods or purchased commercially (Research Diagnostics Inc. Catalog No. RDI-3113, rhuBAFF, Flanders, N.J.) as well as generated synthetically.

The phrase "biological property", "biological characteristic", and the term "activity" in reference to an antibody of the present invention are used interchangeably herein and include, but are not limited to, epitope affinity and specificity (e.g., anti-hTNFSF13b human antibody binding to hTNFSF13b), ability to antagonize the activity of the targeted polypeptide (e.g., TNFSF13b activity), the in vivo stability of the antibody, and the immunogenic properties of the antibody. Other identifiable biological properties or characteristics of an antibody recognized in the art include, for example, cross-reactivity, (i.e., with non-human homologs of the targeted polypeptide, or with other proteins or tissues, generally), and ability to preserve high expression levels of protein in mammalian cells. The aforementioned properties or characteristics can be observed or measured using art-recognized techniques including, but not limited to ELISA, competitive ELISA, surface plasmon resonance analysis, in vitro and in vivo neutralization assays (e.g., Example 2), and immunohistochemistry with tissue sections from different sources including human, primate, or any other source as the need may be. Particular activities and biological properties of anti-hTNFSF13b human antibodies are described in further detail in the Examples below.

The phrase "contact position" includes an amino acid position in the CDR1, CDR2 or CDR3 of the heavy chain variable region or the light chain variable region of an antibody which is occupied by an amino acid that contacts antigen. If a CDR amino acid contacts the antigen, then that amino acid can be considered to occupy a contact position.

"Conservative substitution" or "conservative amino acid substitution" refers to amino acid substitutions, either from natural mutations or human manipulation, wherein the antibodies produced by such substitutions have substantially the same (or improved or reduced, as may be desirable) activity(ies) as the antibodies disclosed herein.

The term "epitope" as used herein refers to a region of a protein molecule to which an antibody can bind. An "immunogenic epitope" is defined as the part of a protein that elicits an antibody response when the whole protein is the immunogen.

The term "binds" as used herein, generally refers to the interaction of the antibody to the epitope of the antigen. More specifically, the term "binds" relates to the affinity of the antibody to the epitope of the antigen. Affinity is measured by $K_D$.

The term "inhibit" or "inhibiting" includes the generally accepted meaning, which includes neutralizing, prohibiting, preventing, restraining, slowing, stopping, or reversing progression or severity of a disease or condition.

The term "neutralizing" or "antagonizing" in reference to an anti-TNFSF13b antibody or the phrase "antibody that antagonizes TNFSF13b activity" is intended to refer to an antibody or antibody fragment whose binding to TNFSF13b results in inhibition of a biological activity induced by TNFSF13b polypeptides. Inhibition of TNFSF13b biological activity can be assessed by measuring one or more in vitro or in vivo indicators of TNFSF13b biological activity including, but not limited to, TNFSF13b-induced proliferation, TNFSF13b-induced immunoglobulin secretion, TNFSF13b-induced prevention of B cell apoptosis, or inhibition of receptor binding in a TNFSF13b receptor binding assay. Indicators of TNFSF13b biological activity can be assessed by one or more of the several in vitro or in vivo assays known in the art. (see, for example, Moore, P. A., et al., Science, 285:260-263 (1999); Schneider, P., et al., *J. Exp. Med.*, 189:1747-1756 (1999); Shu, H., et al., *J. Leuko. Biol.*, 65:680-683 (1999); Mukhopadbyay, A., et al., *J. Biol. Chem.*, 274:15978-15981 (1999); Mackay, F. et al., *J. Exp. Med.*, 190:1697-1710 (1999); Gross, J. A., et al., *Nature*, 404:995-999 (2000); and Example 2). Preferably, the ability of an antibody to neutralize or antagonize TNFSF13b activity is assessed by inhibition of B cell proliferation as shown in Example 2.

The term "$K_{off}$", as used herein, is intended to refer to the off rate constant for dissociation of an antibody from the antibody/antigen complex.

The term "$K_D$", as used herein, is intended to refer to the dissociation constant or the "off" rate divided by the "on" rate, of a particular antibody-antigen interaction. For purposes of the present invention $K_D$ was determined as shown in Example 4

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. Ordinarily, an isolated antibody is prepared by at least one purification step. In preferred embodiments, the antibody will be purified (1) to greater than 95% by weight of antibody as determined by the Lowry method, and most preferably more than 99% by weight, and (2) to homogeneity by SDS-PAGE under reducing or nonreducing conditions using Coomassie blue, or preferably, silver stain. Preferably, an "isolated antibody" is an antibody that is substantially free of other antibodies having different antigenic specificities (e.g., an isolated antibody that specifically binds hTNFSF13b substantially free of antibodies that specifically bind antigens other than hTNFSF13b polypeptide).

The phrase "nucleic acid molecule" includes DNA molecules and RNA molecules. A nucleic acid molecule may be single-stranded or double-stranded, but preferably is double-stranded DNA.

The phrase "isolated nucleic acid molecule", as used herein in reference to nucleic acids encoding antibodies or antibody fragments (e.g., HCVR, LCVR, CDR3) that bind hTNFSF13b polypeptide, includes a nucleic acid molecule in which the nucleotide sequences encoding the antibody, or antibody portion, are free of other nucleotide sequences encoding antibodies or antibody fragments that bind antigens other than hTNFSF13b polypeptide, which other sequences may naturally flank the nucleic acid in human genomic DNA. Thus, for example, an isolated nucleic acid of the invention encoding a HCVR region of an anti-hTNFSF13b human antibody contains no other sequences encoding HCVR regions that bind antigens other than hTNFSF13b polypeptide.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses, and adeno-associated viruses), that serve equivalent functions.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "recombinant" in reference to an antibody includes antibodies that are prepared, expressed, created or isolated by recombinant means. Representative examples include antibodies expressed using a recombinant expression vector transfected into a host cell, antibodies isolated from a recombinant, combinatorial human antibody library, antibodies isolated from an animal (e.g., a mouse) that is transgenic for human immunoglobulin genes or antibodies prepared, expressed, created or isolated by any means that involves splicing of human immunoglobulin gene sequences to other DNA sequences. Such recombinant human antibodies have variable and constant regions derived from human germline immunoglobulin sequences.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Recombinant human antibodies may also be subjected to in vitro mutagenesis (or, when an animal transgenic for human Ig sequences is used, in vivo somatic mutagenesis) and, thus, the amino acid sequences of the HCVR and LCVR regions of the recombinant antibodies are sequences that, while derived from those related to human germline HCVR and LCVR sequences, may not naturally exist within the human antibody germline repertoire in vivo.

Transgenic animals (e.g., mice) that are capable, upon immunization, of producing a full repertoire of human antibodies in the absence of endogenous immunoglobulin production can be employed. Transfer of the human germ-line immunoglobulin gene array in such germ-line mutant mice will result in the production of human antibodies upon antigen challenge (see, e.g., Jakobovits, et al., *Proc. Natl. Acad. Sci. USA*, 90:2551-2555, (1993); Jakobovits, et al., Nature, 362:255-258, (1993; Bruggemann, et al., *Year in Immun.,* 7:33 (1993); *Nature* 148:1547-1553 (1994), *Nature Biotechnology* 14:826 (1996); Gross, J. A., et al., *Nature,* 404:995-999 (2000); and U.S. Pat. Nos. 5,877,397, 5,874,299, 5,814, 318, 5,789,650, 5,770,429, 5,661,016, 5,633,425, 5,625,126, 5,569,825, and 5,545,806 (each of which is incorporated herein by reference in its entirety for all purposes)). Human antibodies can also be produced in phage display libraries (Hoogenboom and Winter, J. Mol. Biol., 227:381 (1992); Marks, et al., J. Mol. Biol., 222:581 (1991)). The techniques of Cole et al. and Boerner, et al. are also available for the preparation of human monoclonal antibodies (Cole, et al., *Monoclonal Antibodies and Cancer Therap*, Alan R. Liss, p. 77 (1985) and Boerner, et al., *J. Immunol.,* 147(1):86-95 (1991)).

"Container" means any receptacle and closure suitable for storing, shipping, dispensing, and/or handling a pharmaceutical product.

"Packaging material" means a customer-friendly device allowing convenient administration and/or ancillary devices that aid in delivery, education, and/or administration. The packaging material may improve antibody administration to the patient, reduce or improve educational instruction time for the patient, provide a platform for improved health economic studies, and/or limit distribution channel workload. Also, the packaging material may include but not be limited to a paper-based package, shrink wrapped package, see-through top packaging, trial-use coupons, educational materials, ancillary supplies, and/or delivery device.

"Package insert" means information accompanying the product that provides a description of how to administer the product, along with the safety and efficacy data required to allow the physician, pharmacist, and patient to make an informed decision regarding use of the product, and/or patient education information. The package insert generally is regarded as the "label" for a pharmaceutical product.

A "subject" means a mammal; preferably a human in need of a treatment. In regards to the present invention subjects in need of treatment include mammals that are suffering from, or are prone to suffer from a disorder in which TNFSF13b activity is detrimental, for example immune diseases, including autoimmune diseases, and inflammatory diseases. Preferred disorders include, but are not limited to, systemic lupus erythematosus, rheumatoid arthritis, juvenile chronic arthritis, Lyme arthritis, Crohn's disease, ulcerative colitis, inflammatory bowel disease, asthma, allergic diseases, psoriasis, graft versus host disease, organ transplant rejection, acute or chronic immune disease associated with organ transplantation, sarcoidosis, infectious diseases, parasitic diseases, female infertility, autoimmune thrombocytopenia, autoimmune thyroid disease, Hashimoto's disease, Sjogren's syndrome, and cancers, particularly B or T cell lymphomas or myelomas.

Various aspects of the invention are described in further detail in the following subsections.

The present invention relates to human monoclonal antibodies that are specific for and neutralize bioactive hTNFSF13b polypeptides. Also disclosed are antibody heavy and light chain amino acid sequences which are highly specific for and neutralize TNFSF13b polypeptides when they are bound to them. This high specificity enables the anti-hTNFSF13b human antibodies, and human monoclonal antibodies with like specificity, to be immunotherapy of TNFSF13b associated diseases.

In one aspect, the invention provides an isolated human antibody comprising at least one of the amino acid sequences shown in SEQ ID NOS: 2, 4, 6, 8, 10, 12, 14, or 16 and that binds a TNFSF13b polypeptide epitope with high affinity, dissociates from a bound TNFSF13b polypeptide with a low $K_{off}$ rate constant of $1\times10^{-4}$ s$^{-1}$ or less, and has the capacity to antagonize TNFSF13b polypeptide activity. In one embodiment, the anti-hTNFSF13b human antibody comprises a polypeptide selected from the group consisting of: CDR1 polypeptide of the LCVR as shown in SEQ ID NO: 4; CDR2 polypeptide of the LCVR as shown in SEQ ID NO: 6; CDR3 polypeptide of the LCVR as shown in SEQ ID NO: 8; CDR1 polypeptide of the HCVR as shown in SEQ ID NO: 12; CDR2 polypeptide of the HCVR as shown in SEQ ID NO: 14; and CDR3 polypeptide of the HCVR as shown in SEQ ID NO: 16. In another embodiment, the anti-hTNFSF13b human antibody comprises at least two of the polypeptides selected from the group consisting of: CDR1 polypeptide of the LCVR as shown in SEQ ID NO: 4; CDR2 polypeptide of the LCVR as shown in SEQ ID NO: 6; CDR3 polypeptide of the LCVR as shown in SEQ ID NO: 8; CDR1 polypeptide of the HCVR as shown in SEQ ID NO: 12; CDR2 polypeptide of the HCVR as shown in SEQ ID NO: 14; and CDR3 polypeptide of the HCVR as shown in SEQ ID NO: 16. In another embodiment, the anti-hTNFSF13b human antibody comprises at least three of the polypeptides selected from the group consisting of: CDR1 polypeptide of the LCVR as shown in SEQ ID NO: 4; CDR2 polypeptide of the LCVR as shown in SEQ ID NO: 6; CDR3 polypeptide of the LCVR as shown in SEQ ID NO: 8; CDR1 polypeptide of the HCVR as shown in SEQ ID NO: 12; CDR2 polypeptide of the HCVR as shown in SEQ ID NO: 14; and CDR3 polypeptide of the HCVR as shown in SEQ ID NO: 16. In another embodiment, the anti-hTNFSF13b human antibody comprises at least four of the polypeptides selected from the group consisting of: CDR1 polypeptide of the LCVR as shown in SEQ ID NO: 4; CDR2 polypeptide of the LCVR as shown in SEQ ID NO: 6; CDR3 polypeptide of the LCVR as shown in SEQ ID NO: 8; CDR1 polypeptide of the HCVR as shown in SEQ ID NO: 12; CDR2 polypeptide of the HCVR as shown in SEQ ID NO: 14; and CDR3 polypeptide of the HCVR as shown in SEQ ID NO: 16. In another embodiment, the anti-hTNFSF13b human antibody comprises at least five of the polypeptides selected from the group consisting of: CDR1 polypeptide of the LCVR as shown in SEQ ID NO: 4; CDR2 polypeptide of the LCVR as shown in SEQ ID NO: 6; CDR3 polypeptide of the LCVR as shown in SEQ ID NO: 8; CDR1 polypeptide of the HCVR as shown in SEQ ID NO: 12; CDR2 polypeptide of the HCVR as shown in SEQ ID NO: 14; and CDR3 polypeptide of the HCVR as shown in SEQ ID NO: 16. In another embodiment, the anti-hTNFSF13b human antibody comprises the polypeptides of CDR1 polypeptide of the LCVR as shown in SEQ ID NO: 4; CDR2 polypeptide of the LCVR as shown in SEQ ID NO: 6; CDR3 polypeptide of the LCVR as shown in SEQ ID NO: 8; CDR1 polypeptide of the HCVR as shown in SEQ ID NO: 12; CDR2 polypeptide of the HCVR as shown in SEQ ID NO: 14; and CDR3 polypeptide of the HCVR as shown in SEQ ID NO: 16.

More preferred, the anti-hTNFSF13b human antibody comprises a light chain variable region (LCVR) polypeptide as shown in SEQ ID NO: 2 or a heavy chain variable region (HCVR) polypeptide as shown in SEQ ID NO: 10. Even more preferred, the anti-hTNFSF13b human antibody comprises the LCVR polypeptide as shown in SEQ ID NO: 2 and the HCVR polypeptide as shown in SEQ ID NO: 10.

In preferred embodiments, the isolated human antibody dissociates from a bound TNFSF13b polypeptide with a $K_{off}$ rate constant of $5\times10^{-5}$ s$^{-1}$ or less, and inhibits TNFSF13b induced proliferation in an in vitro neutralization assay with an IC$_{50}$ of $1\times10^{-7}$ M or less. In more preferred embodiments, the isolated human antibody dissociates from a bound TNFSF13b polypeptide epitope with a $K_{off}$ rate constant of $1\times10^{-5}$ s$^{-1}$ or less and inhibits TNFSF13b induced proliferation in an in vitro neutralization assay with an IC$_{50}$ of $1\times10^{-8}$ M or less. In an even more preferred embodiment, the isolated anti-TNFSF13b human antibody dissociates from a bound hTNFSF13b polypeptide with a $K_{off}$ rate constant of $5\times10^{-6}$ s$^{-1}$ or less and inhibits TNFSF13b induced proliferation in an in vitro assay with an IC$_{50}$ of $1\times10^{-9}$ M or less. Examples of anti-hTNFSF13b human antibodies that meet, the aforementioned kinetic and neutralization criteria include 4A5-3.1.1-B4 antibodies.

The most preferred anti-hTNFSF13b human antibody of the present invention is referred to herein as 4A5-3.1.1-B4. 4A5-3.1.1-B4 has LCVR and HCVR polypeptide sequences as shown in SEQ ID NO:2 and SEQ ID NO: 10, respectively. The poly-nucleotide sequence encoding the LCVR and HCVR of 4A5-3.1.1-B4 is shown in SEQ ID NO: 1 and SEQ ID NO:9, respectively. The properties of the anti-hTNFSF13b human antibodies of the present invention are specifically disclosed in the Examples. Particularly notable is the high affinity for TNFSF13b polypeptide, slow dissociation kinetics, and high capacity to antagonize TNFSF13b polypeptide activity demonstrated by 4A5-3.1.1-B4.

The $K_{off}$ of an anti-hTNFSF13b human antibody can be determined by surface plasmon resonance as generally described in Example 4. Generally, surface plasmon resonance analysis measures real-time binding interactions between ligand (recombinant TNFSF13b polypeptide immobilized on a biosensor matrix) and analyte (antibodies in solution) by surface plasmon resonance (SPR) using the BIAcore system (Pharmacia Biosensor, Piscataway, N.J.). SPR analysis can also be performed by immobilizing the analyte (antibodies on a biosensor matrix) and presenting the ligand (recombinant TNFSF13b in solution).

In one aspect, the present invention is also directed to the cell lines which produce the anti-hTNFSF13b human antibodies of the present invention. The isolation of cell lines producing monoclonal antibodies of the invention can be accomplished using routine screening techniques known in the art. A hybridoma which produces an anti-hTNFSF13b human antibody of the present invention has been deposited with ATCC, (ATCC PTA-3674) as disclosed herein.

A wide variety of host expression systems can be used to express the antibodies of the present invention including bacterial, yeast, baculoviral, plant, and mammalian expression systems (as well as phage display expression systems). An example of a suitable bacterial expression vector is pUC119 (Sfi). Other antibody expression systems are also known in the art and are contemplated herein.

An antibody of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell. Preferably, the recombinant antibodies are secreted into the medium in which the host cells are cultured, from which medium the antibodies can be recovered. Standard recombinant DNA methodologies are used to obtain antibody heavy and light chain genes, incorporate these genes into recombinant expression vectors, and introduce the vectors into host cells.

The isolated DNA encoding the HCVR region can be converted to a full-length heavy chain gene by operatively linking the HCVR-encoding DNA to another DNA molecule encoding heavy chain constant regions (CH1, CH2, and CH3). The DNA sequences of human heavy chain constant region genes are known in the art and DNA fragments encompassing these regions can be obtained by standard PCR amplification.

The heavy chain constant region can be an IgG1, IgG2, IgG3, IgG4, IgA, IgE, IgM or IgD constant region and any allotypic variant therein as described in Kabat, (Kabat, et al, *Sequences of Proteins of Immunological Interest, Fifth Edition*, U.S. Department of Health and Human Services, NIH Publication No. 91-3242 (1991)), but most preferably is an IgG1, or IgG4 constant region. Alternatively, the antibody portion can be an Fab fragment, a Fab' fragment, F(ab')2, or a single chain FV fragment. For a Fab fragment heavy chain gene, the HCVR-encoding DNA can be operatively linked to another DNA molecule encoding only the heavy chain CH1 constant region.

The isolated DNA encoding the LCVR region can be converted to a full-length light chain gene (as well as a Fab light chain gene) by operatively linking the LCVR-encoding DNA to another DNA molecule encoding the light chain constant region, CL. The DNA sequences of human light chain constant region genes are known in the art and DNA fragments encompassing these regions can be obtained by standard PCR amplification. The light chain constant region can be a kappa or lambda constant region.

To create a scFV gene, the HCVR- and LCVR-encoding DNA fragments are operatively linked to another fragment encoding a flexible linker, e.g., encoding the amino acid sequence Gly-Gly-Gly-Gly-Ser-Gly-Gly-Gly-Gly-Ser-Gly-Gly-Gly-Gly-Ser (Gly4-Ser)3, SEQ ID NO: 20, such that the HCVR and LCVR sequences can be expressed as a contiguous single-chain protein, with the LCVR and HCVR regions joined by the flexible linker (see e.g., Bird et al. *Science* 242:423-426 (1988); Huston, et al., *Proc. Natl. Acad Sci. USA* 85:5879-5883 (1988); McCafferty, et al., *Nature* 348:552-554 (1990)).

To express the antibodies of the invention, DNAs encoding partial or full-length light and heavy chains, obtained as described above, are inserted into expression vectors such that the genes are operatively linked to transcriptional and translational control sequences. The antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Additionally, or alternatively, the recombinant expression vector can encode a signal peptide that facilitates secretion of the anti-hTNFSF13b human antibody chain from a host cell. The anti-hTNFSF13b human antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. Regulatory sequences comprise promoters, enhancers and other expression control elements (e.g., polyadenylation signals) that control the transcription or translation of the antibody chain genes. It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced. For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Preferred mammalian host cells for expressing the recombinant antibodies of the invention include Chinese Hamster Ovary (CHO cells) (including dhfr-CHO cells, described in Urlaub and Chasin, *Proc. Natl. Acad. Sci. USA*, 77:4216-4220 (1980), used with a DHFR selectable marker, e.g., as described in R. J. Kaufman and P. A. Sharp, *Mol. Biol.*, 159:601-621 (1982)), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce portions of intact antibodies, such as Fab fragments of scFV molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNFSF13b. The molecules expressed from such truncated DNA molecules are also encompassed by the antibodies of the invention. In a one system for recombinant expression of an antibody of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Antibodies or antigen-binding portions thereof of the invention can be expressed in an animal (e.g., a mouse) that is transgenic for human immunoglobulin genes (see e.g., Taylor, L. D., et al. Nucl. Acids Res., 20:6287-6295 (1992)). Plant cells can also be modified to create transgenic plants that express the antibody or antigen binding portion thereof, of the invention.

In view of the foregoing, another aspect of the invention pertains to nucleic acids, vectors, and host cell compositions that can be used for recombinant expression of the antibodies and antibody portions of the invention. Preferably, the invention features isolated nucleic acids that encode CDRs of 4A5-3.1.1-B4, or the full heavy and/or light chain variable region of 4A5-3.1.1-B4. Accordingly, in one embodiment, the invention features an isolated nucleic acid encoding an antibody heavy chain variable region that encodes the 4A5-3.1.1-134 heavy chain CDR3 comprising the amino acid sequence of SEQ ID NO: 16. Preferably, the nucleic acid encoding the antibody heavy chain variable region further encodes a 4A5-3.1.1-B4 heavy chain CDR2 which comprises the amino acid sequence of SEQ ID NO: 14. More preferably, the nucleic acid encoding the antibody heavy chain variable region further encodes a 4A5-3.1.1-B4 heavy chain CDR1 which comprises the amino acid sequence of SEQ ID NO: 12. Even more preferably, the isolated nucleic acid encodes an antibody heavy chain variable region comprising the amino acid sequence of SEQ ID NO: 10 (the full HCVR region of 4A5-3.1.1-B4).

In other embodiments, the invention features an isolated nucleic acid encoding an antibody light chain variable region that encodes the 4A5-3.1.1-B4 light chain CDR3 comprising the amino acid sequence of SEQ ID NO:8 Preferably, the nucleic acid encoding the antibody light chain variable region further encodes a 4A5-3.1.1-B4 light chain CDR1 which comprises the amino acid sequence of SEQ ID NO:4. Even more preferably, the isolated nucleic acid encodes an antibody light chain variable region comprising the amino acid sequence of SEQ ID NO:2 (the full LCVR region of 4A5-3.1.1-B4).

In other embodiments, the invention features an isolated nucleic acid encoding an antibody light chain variable region that encodes the 4A5-3.1.1-B4 light chain CDR3 comprising the amino acid sequence of SEQ ID NO:8 Preferably, the nucleic acid encoding the antibody light chain variable region further encodes a 4A5-3.1.1-B4 light chain CDR1 which comprises the amino acid sequence of SEQ ID NO:4. Even more preferably, the isolated nucleic acid encodes an antibody light chain variable region comprising the amino acid sequence of SEQ ID NO:2 (the full LCVR region of 4A5-3.1.1-B4).

In another embodiment, the invention provides an isolated nucleic acid encoding a heavy chain CDR3 domain comprising the amino acid sequence of SEQ ID NO: 16 (i.e., the 4A5-3.1.1-B4 HCVR CDR3). This nucleic acid can encode only the CDR3 region or, more preferably, encodes an entire antibody heavy chain variable region (HCVR). For example, the nucleic acid can encode a HCVR having a CDR2 domain comprising the amino acid sequence of SEQ ID NO:14 (i.e., the 4A5-3.1.1-B4 HCVR CDR2) and a CDR1 domain comprising the amino acid sequence of SEQ ID NO:12 (i.e., 4A5-3.1.1-B4 HCVR CDR1).

In still another embodiment, the invention provides an isolated nucleic acid encoding an antibody light chain variable region comprising the amino acid sequence of SEQ ID NO:2 (i.e., the 4A5-3.1.1-B4 LCVR). Preferably this nucleic acid comprises the nucleotide sequence of SEQ ID NO:1, although the skilled artisan will appreciate that due to the degeneracy of the genetic code, other nucleotide sequences can encode the amino acid sequence of SEQ ID NO:2. The nucleic acid can encode only the LCVR or can also encode an antibody light chain constant region, operatively linked to the LCVR. In one embodiment, this nucleic acid is in a recombinant expression vector.

In still another embodiment, the invention provides an isolated nucleic acid encoding an antibody heavy chain variable region comprising the amino acid sequence of SEQ ID NO:10 (i.e., the 4A5-3.1.1-B4 HCVR). Preferably this nucleic acid comprises the nucleotide sequence of SEQ ID NO:9, although the skilled artisan will appreciate that due to the degeneracy of the genetic code, other nucleotide sequences can encode the amino acid sequence of SEQ ID NO: 10. The nucleic acid can encode only the HCVR or can also encode a heavy chain constant region, operatively linked to the HCVR. For example, the nucleic acid can comprise an IgG1 or IgG4 constant region. In one embodiment, this nucleic acid is in a recombinant expression vector.

Those of ordinary skill in the art are aware that modifications in the amino acid sequence of the antibody can result in an antibody that display equivalent or superior functional characteristics when compared to the original antibody. Alterations in the antibodies of the present invention can include one or more amino acid insertions, deletions, substitutions, truncations, fusions, and the like, either from natural mutations or human manipulation. The present invention encompasses antibodies disclosed herein further comprising one or more amino acid substitutions provided that the substituted antibodies have substantially the same (or improved or reduced, as may be desirable) activity(ies) as the antibodies disclosed herein. Preferably, a CDR of the present invention has 3 or less conservative substitutions. Preferably, a CDR of the present invention has 2 or less conservative substitutions. Preferably, a CDR of the present invention has one conservative substitution. The skilled artisan will recognize that antibodies having conservative amino acid substitutions can be prepared by a variety of techniques known in the art. For example, a number of mutagenesis methods can be used, including PCR assembly, Kunkel (dut-ung-) and thiophosphate (Amersham Sculptor kit) oligonucleotide-directed mutagenesis. Conservative substitutions of interest are shown in Table 1 along with preferred substitutions.

TABLE 1

Conservative Substitutions

| Residue | Substitutions | Preferred Substitution |
|---|---|---|
| Ala (A) | gly, val, leu, ile, ser, met, thr | Val |
| Arg (R) | lys, gln, asn, his | Lys |
| Asn (N) | Gln | Gln |
| Asp (D) | Glu | Glu |
| Cys (C) | Ser | Ser |
| Gln (O) | Asn | Asn |
| Glu (E) | Asp | Asp |
| Gly (G) | Ala, ile, leu, pro, ser, met, val val | Ala |
| His (H) | Asn, gln, lys, arg | Arg |
| Ile (I) | Leu, val, met, ala, phe, norleucine | Leu |
| Leu (L) | norleucine, ile, val, met, ala phe | Ile |
| Lys (K) | Arg, gln, asn, his | Arg |
| Met (M) | Ala, gly, ile, leu, phe, ser, val | Leu |
| Phe (F) | Leu, val, ile, ala, trp, tyr | Tyr |
| Pro (P) | | |
| Ser (S) | Ala, gly, ile, leu, met, thr, val | Thr |
| Thr (T) | Ala, gly, ile, leu, met, ser, val | Ser |
| Trp (W) | tyr, phe | Tyr |
| Tyr (Y) | trp, phe, thr, ser | Phe |
| Val (V) | Ala, ile, leu, met, ser, met, norleu | Leu |

The invention also provides recombinant expression vectors encoding an antibody comprising a polypeptide selected from the group consisting of a polypeptide as shown in SEQ ID NO: 2, a polypeptide as shown in SEQ ID NO: 4, a polypeptide as shown in SEQ ID NO: 6, a polypeptide as shown in SEQ ID NO: 8, a polypeptide as shown in SEQ ID NO: 10, a polypeptide as shown in SEQ ID NO: 12, a polypeptide as shown in SEQ ID NO: 14; and a polypeptide as shown in SEQ ID NO: 16.

The invention also provides recombinant expression vectors encoding both an antibody heavy chain and an antibody light chain. For example, in one embodiment, the invention provides a recombinant expression vector encoding:

a) an antibody heavy chain having a variable region comprising the amino acid sequence of SEQ ID NO:10; and b) an antibody light chain having a variable region comprising the amino acid sequence of SEQ ID NO:2.

Once expressed, the whole antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis and the like. Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically or prophylactically, as directed herein.

The antibodies of the present invention can be incorporated into pharmaceutical compositions suitable for administration to a subject. Typically, the pharmaceutical composition comprises an antibody or antibody portion of the invention and a pharmaceutically acceptable diluent, carrier, and/or excipient. The pharmaceutical compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents and the like are used as appropriate.

A pharmaceutical composition comprising an anti-hTNFSF13b human antibody of the present invention can be administered to a mammal at risk for or exhibiting autoimmunity related symptoms or pathology such as systemic lupus erythematosus using standard administration techniques by intravenous, intraperitoneal, subcutaneous, pulmonary, transdermal, intramuscular, intranasal, buccal, sublingual, or suppository administration.

The antibodies of the invention can be incorporated into a pharmaceutical composition suitable for parenteral administration. Peripheral systemic delivery by intravenous or intraperitoneal or subcutaneous injection is preferred. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer.

The pharmaceutical compositions typically must be sterile and stable under the conditions of manufacture and storage. Therefore, pharmaceutical compositions may be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration. Therapeutic agents of the invention can all be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 6 and 8 is tolerated.

TNFSF13b plays a critical role in the pathology associated with a variety of diseases involving immune and inflammatory factors. Therefore, a pharmaceutical composition comprising an anti-hTNFSF13b human antibody of the invention can be used to treat disorders in which TNFSF13b activity is detrimental, for example immune diseases including autoimmune diseases and inflammatory diseases. Preferred disorders include, but are not limited to, systemic lupus erythematosus, rheumatoid arthritis, juvenile chronic arthritis, Lyme arthritis, Crohn's disease, ulcerative colitis, inflammatory bowel disease, asthma, allergic diseases, psoriasis, graft versus host disease, organ transplant rejection, acute or chronic immune disease associated with organ transplantation, sarcoidosis, infectious diseases, parasitic diseases, female infertility, autoimmune thrombocytopenia, autoimmune thyroid disease, Hashimoto's disease, Sjogren's syndrome, and cancers, particularly B or T cell lymphomas or myelomas.

More preferably, a pharmaceutical composition comprising an anti-hTNFSF13b human antibody and/or antibody fragment of the invention is used to treat systemic lupus erythematosus.

The use of the antibody of an anti-hTNFSF13b human antibody of the present invention in the manufacture of a medicament for the treatment of at least one of the aforementioned disorders in which TNFSF13b activity is detrimental is also contemplated herein.

In certain situations, an antibody of the invention will be co-formulated with and/or co-adminstered with one or more additional therapeutic agents that are used in the treatment of autoimmune and/or inflammatory diseases. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

The pharmaceutical compositions of the invention may include a "therapeutically effective amount" or a "prophylactically effective amount" of an antibody of the invention. A "therapeutically effective amount" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation.

Given their ability to bind to hTNFSF13b, antibodies, of the invention can be used to detect TNFSF13b polypeptides (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting TNFSF13b in a biological sample comprising contacting a biological sample with an antibody, or antibody portion, of the invention and detecting either the antibody (or antibody portion) bound to hTNFSF13b or unbound antibody (or antibody portion), to thereby detect hTNFSF13b in the biological sample. The antibody is directly or indirectly labeled with a detectable substance to facilitate detection of the bound or unbound antibody. Suitable detectable substances include various enzymens, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinyl-amine fluorescein, dansyl chloride or phycoerythrin; an example of a luminescent material includes luminol; and examples of suitable radioactive material include $^{125}I$, $^{131}I$, $^{35}S$, or $^{3}H$.

Alternative to labeling the antibody, TNFSF13b can be assayed in biological fluids by a competition immunoassay utilizing TNFSF13b standards labeled with a detectable substance and an unlabeled anti-hTNFSF13b human antibody. In this assay, the biological sample, the labeled TNFSF13b standards and the anti-hTNFSF13b human antibody are combined and the amount of labeled TNFSF13b standard bound to the unlabeled antibody is determined. The amount of TNFSF13b in the biological sample is inversely proportional to the amount of labeled rTNFSF13b standard bound to the anti-hTNFSF13b human antibody.

In another embodiment, the present invention provides a use of an anti body that neutralizes TNFSF13b activity by binding an epitope of TNFSF13b. The epitope was identified as described in Example 10. For reference, the soluble portion of hTNFSF13b is represented as follows:

```
Human TNFSF13b
  1 AVQGPEETVI QDCLQLIADS ETPTIQKGSY TFVPWLLSFK   40

41 RGSALEEKEN KILVKETGYF FIYGQVLYTD KTYANGHLIQ   80

81 RKKVHVFGDE LSLVTLFRCI QNMPETLPNN SCYSAGIAKL  120

121 EEGDELOLAI PRENAQISLD GDVTFFGALK LL          152
SEQ ID NO: 21."
```

The hTNFSF13b amino acids involved in binding the novel anti-hTNFSF13b human antibodies comprise at least one of the amino acids selected from the group consisting of: threonine at position 69, lysine at position 71, threonine at position 72, tyrosine at position 73, glutamic acid at position 105, threonine at position 106, leucine at position 107, and asparagine at position 109. In another embodiment, the amino acids involved in binding the novel anti-hTNFSF13b human antibodies comprise at least two of the amino acids selected from the group consisting of: threonine at position 69, lysine at position 71, threonine at position 72, tyrosine at position 73, glutamic acid at position 105, threonine at position 106, leucine at position 107, and asparagine at position 109. In another embodiment, the amino acids involved in binding the novel anti-hTNFSF13b human antibodies comprise at least three of the amino acids selected from the group consisting of: threonine at position 69, lysine at position 71, threonine at position 72, tyrosine at position 73, glutamic acid at position 105, threonine at position 106, leucine at position 107, and asparagine at position 109. In another embodiment, the amino acids involved in binding the novel anti-hTNFSF13b human antibodies comprise at least four of the amino acids selected from the group consisting of: threonine at position 69, lysine at position 71, threonine at position 72, tyrosine at position 73, glutamic acid at position 105, threonine at position 106, leucine at position 107, and asparagine at position 109.

In another embodiment, the amino acids involved in binding the novel anti-hTNFSF13b human antibodies comprise lysine at position 71, threonine at position 72, tyrosine at position 73, and glutamic acid at position 105.

In another embodiment, the amino acids involved in binding the novel anti-hTNFSF13b human antibodies comprise glutamic acid at position 105 and at least one of the amino acids selected from the group consisting of: threonine at position 69, lysine at position 71, threonine at position 72, and tyrosine at position 73. In another embodiment, the amino acids involved in binding the novel anti-hTNFSF13b human antibodies comprise threonine at position 106 and at least one of the amino acids selected from the group consisting of: threonine at position 69, lysine at position 71, threonine at position 72, and tyrosine at position 73. In another embodiment, the amino acids involved in binding the novel anti-hTNFSF13b human antibodies comprise leucine at position 107 and at least one of the amino acids selected from the group consisting of: threonine at position 69, lysine at position 71, threonine at position 72, and tyrosine at position 73. In another embodiment, the amino acids involved in binding the novel anti-hTNFSF13b human antibodies comprise asparagine at position 109 and at least one of the amino acids selected from the group consisting of: lysine at position 71, threonine at position 72, and tyrosine at position 73.

In another embodiment, the amino acids involved in binding the novel anti-hTNFSF13b human antibodies comprise lysine at position 71, threonine at position 72, tyrosine at position 73, and glutamic acid at position 105.

The following examples are intended to illustrate but not to limit the invention.

EXAMPLE 1

Generation of Anti-hTNFSF13b Human Monoclonal Antibodies

Monoclonal antibodies were generated using the HuMAb-Mouse technology at Medarex by immunizing the mice with soluble hTNFSF13b (amino acids 133-285, purchased from RDI, Flanders, N.J.). Both the HCo7 and HCo12 mice were used. Mice were immunized with 15 μg to 50 μg soluble hTNFSF13b in RIBI, Freund's complete adjuvant or Freund's incomplete adjuvant. Eight mice producing serum antibody titers to hTNFSF13b were injected i.v. with 10 μg hTNFSF13b in PBS. The spleen was harvested three days later from each mouse and fused with myeloma cells according to the method described in Zola (Zola, H. Monoclonal antibodies: A Manual of Techniques. CRC Press, Boca Raton, Fla. (1987)).

Hybridomas were tested for binding to hTNFSF13b and to make sure they were expressing human immunoglobulin heavy and light chains. Antibody binding to hTNFSF13b was detected by ELISA as follows:

Plates were coated with 50 μl of 5 μg/ml hTNFSF13b in PBS overnight at 4° C. Plates were then emptied and blocked with 100 μl PBS+0.05% Tween 20 (PBST)+5% chicken serum for 1 hour at room temperature. After washing three times with PBST, the plates were drained and 100 μl diluted secondary reagents (HRP-HuIgGFc, Jackson cat#109-036-098 or HRP-HuKappa, Bethyl cat#A80-115P; 1:5000 in blocking buffer) was added per well. After an 1 hour incubation at room temperature plates were washed three times as described above. Plates were developed using 10 ml citrate phosphate buffer pH 4.0, 80 μl ABTS, 8 μl $H_2O_2$ per plate. After incubating 30 min. to 1 hour at room temperature, absorbance of the plates was read A415-A490. Hybridomas that showed binding to hTNFSF13b and that were huIgG heavy chain and human kappa light chain were selected for subcloning.

Cell culture media of subcloned hybridomas was concentrated in Amicon ProFlux M12 tangential filtration systems using an Amicon S3Y30 UF membranes. The concentrated media was passed over protein-A Sepharose columns (5 to 20 ml column) at a flow rate of 5 ml/min. The columns were washed with buffer A (PBS, pH 7.4) until the absorbance returned to baseline and the bound polypeptides were eluted with 50 mM citric acid, pH 3.2. Fractions were immediately neutralized with 1M Tris, pH 8.0. Fractions were then analyzed by SDS-PAGE. Fractions containing antibody were pooled and concentrated using an Ultrafree™ centrifugal filter unit (Millipore, 10 kDa molecular weight cut-off).

EXAMPLE 2

Functional Activity of Anti-hTNFSF13b Human Antibodies

Neutralizing activity of the anti-hTNFSF13b human antibodies of the invention was measured using a murine Il-1 dependent B cell line, T1165.17. The cells were washed three times with assay media (RPMI1640 containing 1000 FBS, 1 mM sodium pyruvate, $5\times10^{-5}$ M 2-mercaptoethanol and penicillin, streptomycin and fungizone) to remove IL-1. The cells were resuspended at 100,000 cells/ml in assay media containing 2.5 ng/ml soluble huTNFSF13b and plated at 5000 cells/well in a 96 well plate and incubated at 37° C. in 5% $CO_2$. Supernatants from ELISA positive hybridomas were included at a 1:4 dilution. Forty-eight hours later, 20 μl of Promega™ CellTiter 96™ Aqueous One Solution (Madison, Wis.) was added and the plate incubated for 5 more hours at 37° C. in 5% $CO_2$. Absorbance was read at A490, to measure proliferation. An example of neutralization activity for one of the hybridoma supernatants, 4A5-3.1.1-B4, is shown in FIG. 1. As a control, the antibodies were added to IL-1 stimulated cells. There was no evidence of inhibition of IL-1 stimulated proliferation, only the hTNFSF13b stimulated proliferation.

The neutralizing antibodies were tested for the ability to inhibit TNFSF13b augmented primary human B cell proliferation in response to anti-IgM stimulation. Primary human B cells were isolated from human blood using CD19 positive selection using the MACS magnetic isolation system (Miltenyi Biotec, Auburn, Calif.). The B cells were added to wells of a 96-well plate at $2\times10^5$ cells per well in complete RPMI containing 10% FCS (complete RPMI is RPMI1640 containing 10 mM L-glutamine, 100 U/ml penicillin, 100 μg/ml streptomycin, 1 mM sodium pyruvate, 0.1 mM non-essential amino acids, and $1\times10^{-5}$ M β-mercaptoethanol). Some of the wells were coated with 10 μg/ml anti-human IgM in PBS (BD PharMingen, Clone G20-127), overnight at 4° C. and washed four times with PBS before use. Some of the cells were stimulated with soluble hTNFSF13b (25 ng/ml) in the presence or absence of neutralizing anti-hTNFSF13b antibody (2.5 µg/ml). FIG. 2 illustrates the ability of 4A5-3.1.1-B4 to neutralize the stimulatory effect of hTNFSF13b.

EXAMPLE 3

Characterization of Monoclonal Antibodies

All of the neutralizing anti-hTNFSF13b antibodies were either human IgG1 or human IgG4. They were also assayed for their ability to bind to hTNFSF13b in a denatured state, i.e., hTNFSF13b separated on SDS-PAGE and blotted onto nitrocellulose. All of the neutralizing antibodies failed to bind hTNFSF13b in a Western blot while several of the non-neutralizing antibodies were able to do so.

Experiments utilizing the BIACore™ system were performed to determine if non-neutralizing antibodies and neutralizing antibodies bound to the same site on hTNFSF13b. First, 4A5-3.1.1-B4 was coated onto a chip followed by injection of hTNFSF13b and then a saturating amount of non-neutralizing antibody. Once saturation was achieved, a high concentration of 4A5-3.1.1-B4 was run over the chip. Eleven of the non-neutralizing monoclonal antibodies were unable to compete for the same binding site as 4A5-3.1.1-B4. One non-neutralizing hybridoma was able to block the binding of 4A5-3.1.1-B4 by approximately 45%, indicating that it may have an epitope near the 4A5-3.1.1-B4 epitope.

Using the same experimental design, it was also determined that the neutralizing mAb, 4A5-3.1.1-B4, could compete for the same binding site as one of the receptors for hTNFSF13b, TACI. These experiments suggest that TACI-Fc and 4A5-3.1.1-B4 may have overlapping epitopes on hTNFSF13b.

4A5-3.1.1-B4 was immobilized on a solid phase by passing the antibody solution over an IMAC resin loaded with $Co^{+2}$. Following binding, the cobalt was oxidized to the +3 state by incubation of the resin with a dilute peroxide solution. After washing the resin, native hTNFSF13b and hTNFSF13b that was modified (by reduction/alkylation or by thermal denaturation) was passed over the column. After washing, the bound protein was eluted with an acidic solution and the eluted proteins were analyzed by MALDI MS. 4A5-3.1.1-B4 bound native recombinant hTNFSF13b, but did not bind either the chemically or thermally modified hTNFSF13b. Therefore, the 4A5-3.1.1-B4 appears to recognize a conformational epitope on soluble hTNFSF13b.

Recombinant soluble hTNFSF13b (RDI) was incubated with 4A5-3.1.1-B4 or anti-TNFSF13b rabbit polyclonal antibody (MoBiTec, Marco Island, Fla.; against amino acids 254 to 269 of hTNFSF13b) on ice for 2 hours and the protein mixture was applied to a size-exclusion HPLC (two, tandem TosoHaas TSK-GEL G3000PW columns) equilibrated in PBS at a flow rate of 0.25 ml/min. Proteins were eluted with PBS. As controls, antibody solutions and the solution of hTNFSF13b were analyzed separately. Human TNFSF13b eluted from the size exclusion column in a position consistent with a trimer of TNFSF13b molecules. The elution of trimeric hTNFSF13b shifted to an earlier timepoint in the presence of 4A5-3.1.1-B4 but not in the presence of anti-TNFSF13b polyclonal antibodies indicating the binding of trimeric hTNFSF13b to the 4A5-3.1.1-B4 antibody. This data suggests that the neutralizing mAb 4A5-3.1.1-B4 binds to a conformational epitope on hTNFSF13b.

EXAMPLE 4

Affinity Measurement of Monoclonal Antibodies by BIAcore

The affinity of various anti-hTNFSF13b human antibodies for hTNFSF13b was measured using a BIAcore 2000 instrument system. The system utilizes the optical properties of Surface Plasmon Resonance to detect alteration in protein concentration of interacting molecules within a dextran biosensor matrix. Except where noted, all reagents and materials were purchased from BIAcore AB (Upsala, Sweden). All measurements were performed at 25° C. Samples were dissolved in HBS-EP buffer (150 mM NaCl, 3 mM EDTA, 0.005% (w/v) surfactant P-20, and 10 mM HEPES, pH 7.4). Goat anti-mouse IgG (Fc specific; Jackson Immunoresearch, West Grove, Pa.) was immobilized on flow cell 1 on a CM5 sensor chip using the amine coupling kit. Goat anti-human IgG (Fc specific; Jackson Immunoresearch) was immobilized on flow cell 2 also by amine coupling. Both antibodies were immobilized to reach 700 response units each.

Binding of recombinant hTNFSF13b (Research Diagnostics, Inc., Flanders, N.J.) was evaluated using multiple analytical cycles. Each cycle was performed at a flow rate of 30 µl/min. and consisted of the following steps: injection of 150 µl of 4A5-3.1.1-B4 at 20 µg/ml, injection of 250 µl of hTNFSF13b (starting at 50 nM and using 2 fold serial dilutions for each cycle) followed by 15 minutes for dissociation, and regeneration using 90 µl of 10 mM glycine HCl, pH 1.5.

Association and dissociation rates for each cycle were evaluated using a Langmuir 1:1 binding model in the BIAevaluation software. The $K_D$ of 4A5-3.1.1-B4 for hTNFSF13b was determined to be 38 pM.

EXAMPLE 5

Cloning and Sequencing of Heavy and Light Chain Antigen Binding Regions

The variable region for the heavy and light chain for the neutralizing human mAb 4A5-3.1.1-B4 were cloned and sequenced using the following protocols.

mRNA was prepared from $2\times10^6$ hybridoma cells using the Micro-Fast Track protocol (Invitrogen) supplied with the kit. cDNA was prepared from 200 µl of ethanol precipitate of mRNA using cDNA Cycle kit (Invitrogen) by spinning the aliquot of mRNA for 30 min. at 14,000 rpm at 4° C. followed by washing the pellet with 70% ethanol. The air dried pellet was resuspended in 11.5 µl of sterile water and cDNA was prepared following the kit's instructions. The optional second round of cDNA synthesis was omitted but the cDNA was cleaned using the pheno/chlorform extraction step and ethanol precipitation. The cDNA pellet was resuspended in 30 µl of TE for use in PCR.

The PCR reactions were set up with degenerate primers at the 5' end of the variable region for the heavy and light chain paired with 3' primers in the constant region. For each 50 ul reaction, 1 ul of cDNA was used. The reaction was set up as directed for use with PfuI followed by 20 cycles. The PCR products were checked by running 5 µl of each reaction on a 1% agarose gel. The positive reactions were cloned using the Zero Blunt TOPO PCR cloning kit (Invitrogen). Minipreps from the positive clones were sequenced and analyzed for productive gene rearrangements. Results from independent PCR reactions and sequencing of multiple clones revealed the sequences as described below.

Human antibody 4A5-3.1.1-B4 light chain sequences (CDRs are in bold).

```
      E  I  V     L  T  Q  S     P  A  T     L  S  L     S  P  G  E
  1 GAAATTGTGT TGACGCAGTC TCCAGCCACC CTGTCTTTGT CTCCAGGGGA
    CTTTAACACA ACTGCGTCAG AGGTCGGTGG GACAGAAACA GAGGTCCCCT

CDR1
      R  A  T     L  S  C     R  A  S  Q     S  V  S     R  Y  L
 51 AAGAGCCACC CTCTCCTGCA GGGCCAGTCA GAGTGTTAGC CGCTACTTAG
    TTCTCGGTGG GAGAGGACGT CCCGGTCAGT CTCACAATCG GCGATGAATC

A  W  Y  Q     K  P     G  Q  A     P  R  L  L     I  Y  D
101 CCTGGTACCA GCAGAAACCT GGCCAGGCTC CCAGGCTCCT CATCTATGAT
    GGACCATGGT CGTCTTTGGA CCGGTCCGAG GGTCCGAGGA GTAGATACTA

CDR2
      A  S  N     R  A  T  G     I  P  A  R     F  S     G  S  G  S
151 GCATCCAACA GGGCCACTGG CATCCCAGCC AGGTTCAGTG GCAGTGGGTC
    CGTAGGTTGT CCCGGTGACC GTAGGGTCGG TCCAAGTCAC CGTCACCCAG

G  T  D     S  T  L     T  I  S  S     L  E  P     E  D  F
201 TGGGACAGAC TCCACTCTCA CCATCAGCAG CCTAGAGCCT GAAGATTTTG
    ACCCTGTCTG AGGTGAGAGT GGTAGTCGTC GGATCTCGGA CTTCTAAAAC

CDR3
      A  V  Y  Y     C  Q  Q     R  S  N     W  P  Q  T     F  G  Q
251 CAGTTTATTA CTGTCAGCAG CGTAGCAACT GGCCTCGGAC GTTCGGCCAA
    GTCAAATAAT GACAGTCGTC GCATCGTTGA CCGGAGCCTG CAAGCCGGTT

Ck
      G  T  K     V  E  I  K     R  T  V     A  A  P     S  V  F  I
301 GGGACCAAGG TGGAAATCAA ACGAACTGTG GCTGCACCAT CTGTCTTCAT
    CCCTGGTTCC ACCTTTAGTT TGCTTGACAC CGACGTGGTA GACAGAAGTA

F  P
351 CTTCCCG    SEQ ID NO: 23
    GAAGGGC    SEQ ID NO: 24
```

Human antibody 4A5-3.1.1-B4 heavy chain sequences (CDRs are in bold, signal sequence is italicized).

```
      *M  K  H     L  W  F  F     L  L  L     V  A  A     P  R  W  V*
  1 ATGAAACACC TGTGGTTCTT CCTCCTCCTG GTGGCAGCTC CCAGATGGGT
    TACTTTGTGG ACACCAAGAA GGAGGAGGAC CACCGTCGAG GGTCTACCCA

*L  S*  Q     V  Q  L     Q  Q  W     G  A  G     L  L  K  P
 51 CCTGTCCCAG GTGCAACTAC AGCAGTGGGG CGCAGGACTG TTGAAGCCTT
    GGACAGGGTC CACGTTGATG TCGTCACCCC GCGTCCTGAC AACTTCGGAA

S  E  T  L     S  L  T     C  A  V     Y  G  G     F  S  G
101 CGGAGACCCT GTCCCTCACC TGCGCTGTCT ATGGTGGGTC CTTCAGTGGT
    GCCTCTGGGA CAGGGAGTGG ACGCGACAGA TACCACCCAG GAAGTCACCA

CDR1
      Y  Y  W     S  W  I  R     Q  P  P     G  K  G     L  E  W  I
151 TACTACTGGA GCTGGATCCG CCAGCCCCCA GGGAAGGGGC TGGAGTGGAT
    ATGATGACCT CGACCTAGGC GGTCGGGGGT CCCTTCCCCG ACCTCACCTA

CDR2
      G  E  I     N  H  S     G  S  T  N     Y  N  P     S  L  K
201 TGGGGAAATC AATCATAGTG GAAGCACCAA CTATAATCCG TCCCTCAAG
    ACCCCTTTAG TTAGTATCAC CTTCGTGGTT GATATTAGGC AGGGAGTTC

S  R  V  T     I  S  V     D  T  S     K  N  Q  F     S  L  K
251 GTCGAGTCAC CATATCAGTA GACACGTCCA AGAACCAGTT CTCCCTGAAA
    CAGCTCAGTG GTATAGTCAT CTGTGCAGGT TCTTGGTCAA GAGGGACTTT
```

-continued

```
         L  S  S   V  T  A  A   D  T  A   V  Y  Y   C  A  R  G
301 CTGAGCTCTG TGACCGCCGC GGACACGGCT GTGTATTACT GTGCGAGAGG
    GACTCGAGAC ACTGGCGGCG CCTGTGCCGA TCTTGGTCAA GAGGGACTTT

┌─CDR3─┐
         Y  Y  D   I  L  T   G  Y  Y  Y   Y  F  D   Y  W  G
351 GTATTACGAT ATTTTGACTG GTTATTATTA CTACTTTGAC TACTGGGGCC
    CATAATGCTA ACTGGCGGCG CCTGTGCCGA CACATAATGA CACGCTCTCC

┌──Cγ1──┐
         Q  G  T   L  V  T  V   S  S  A   S  T  K  G   P  S  V
401 AGGGAACCCT GGTCACCGTC TCCTCAGCCT CCACCAAGGG CCCATCGGTC
    TCCCTTGGGA CCAGTGGCAG AGGAGTCGGA GGTGGTTCCC GGGTAGCCAG

F  P  L   A
451 TTCCCCCTGG CA   SEQ ID NO: 25
    AAGGGGGACC GT   SEQ ID NO: 26
```

EXAMPLE 6

Species Crossreactivity of Anti-hTNFSF13b Human Antibodies with Non-Human TNFSF13b In order to determine the species crossreactivity of the neutralizing mAbs, an ELISA was set up utilizing 4A5-3.1.1-B4 as both the capture and detecting mAb. Human recombinant TNFSF13b was used as the standard curve. Human TNFSF13b could be detected in the culture supernatant from CHO cells transfected with a vector expressing hTNFSF13b, supernatants from cultured human monocytes or human serum or plasma. Supernatants from CHO cells expressing murine TNFSF13b were tested for reactivity in the ELISA and were negative. 4A5-3.1.1-B4 was also unable to immunopreciptate murine TNFSF13b but was able to immunoprecipitate human TNFSF13b. Murine TNFSF13b was used in the proliferation assay described in Example 2. Using this proliferation assay, 4A5-3.1.1-B4 was unable to neutralize the proliferation induced by murine TNFSF13b. This indicates that 4A5-3.1.1-B4 is unable to recognize murine TNFSF13b.

EXAMPLE 7

Amino Acid Sequence of Heavy Chain 4A5-3.1.1-B4

Below is the amino acid sequence of the heavy chain 4A5-3.1.1-B4 antibody which comprises the HCVR and the IgG4 constant region. The human IgG4 constant region has a serine at position 231. However, this position at 231 was substituted from a serine to a proline which introduces a structural change in the hinge region for obtaining optimal inter-chain disulfide bonds. This reduces the generation of half antibodies. Half antibodies are formed from one heavy chain and one light chain.

```
  1 QVQLQQWGAG LLKPSETLSL TCAVYGGSFS GYYWSWIRQP PGKGLEWIGE
 51 INHSGSTNYN PSLKSRVTIS VDTSKNQFSL KLSSVTAADT AVYYCARGYY
101 DILTGYYYYF DYWGQGTLVT VSSASTKGPS VFPLAPCSRS TSESTAALGC
151 LVKDYFPEPV TVSWNSGALT SGVHTFPAVL QSSGLYSLSS VVTVPSSSLG
201 TKTYTCNVDH KPSNTKVDKR VESKYGPPCP PCPAPEFLGG PSVFLFPPKP
251 KDTLMISRTP EVTCVVVDVS QEDPEVQFNW YVDGVEVHNA KTKPREEQFN
301 STYRVVSVLT VLHQDWLNGK EYKCKVSNKG LPSSIEKTIS KAKGQPREPQ
351 VYTLPPSQEE MTKNQVSLTC LVKGFYPSDI AVEWESNGQP ENNYKTTPPV
401 LDSDGSFFLY SRLTVDKSRW QEGNVFSCSV MHEALHNHYT QKSLSLSLGK
    (SEQ ID NO: 17)
```

(SEQ ID NO: 17)

In addition, an alanine for phenylalanine substitution at position 237 and an alanine or glutamic acid substitution for leucine at position 238 can be made to lessen the effector function of the antibody.

EXAMPLE 8

Amino Acid Sequence of Heavy Chain 4A5-3.1.1-B4

Below is the amino acid sequence of the heavy chain 4A5-3.1.1-B4 antibody which comprises the HCVR and the IgG1 constant region.

```
  1  QVQLQQWGAG  LLKPSETLSL  TCAVYGGSFS  GYYWSWIRQP  PGKGLEWIGE

51  INHSGSTNYN  PSLKSRVTIS  VDTSKNQFSL  KLSSVTAADT  AVYYCARGYY

101  DILTGYYYYF  DYWGQGTLVT  VSSASTKGPS  VFPLAPSSKS  TSGGTAALGC

151  LVKDYFPEPV  TVSWNSGALT  SGVHTFPAVL  QSSGLYSLSS  VVTVPSSSLG

201  TQTYICNVNH  KPSNTKVDKK  VEPKSCDKTH  TCPPCPAPEL  LGGPSVFLFP

251  PKPKDTLMIS  RTPEVTCVVV  DVSHEDPEVK  FNWYVDGVEV  HNAKTKPREE

301  QYNSTYRVVS  VLTVLHQDWL  NGKEYKCKVS  NKALPAPIEK  TISKAKGQPR

351  EPQVYTLPPS  RDELTKNQVS  LTCLVKGFYP  SDIAVEWESN  GQPENNYKTT

401  PPVLDSDGSF  FLYSKLTVDK  SRWQQGNVFS  CSVMHEALHN  HYTQKSLSLS

451  PGK(SEQ ID NO: 18)
```

(SEQ ID NO: 18)

EXAMPLE 9

Amino Acid sequence of Light Chain 4A5-3.1.1-B4

Below is the amino acid sequence of the light chain 4A5-3.1.1-B4 antibody which comprises the LCVR and the kappa constant region.

```
  1  EIVLTQSPAT  LSLSPGERAT  LSCRASQSVS  RYLAWYQQKP  GQAPRLLIYD

51  ASNRATGIPA  RFSGSGSGTD  STLTISSLEP  EDFAVYYCQQ  RSNWPRTFGQ

101  GTKVEIKRTV  AAPSVFIFPP  SDEQLKSGTA  SVVCLLNNFY  PREAKVQWKV

151  DNALQSGNSQ  ESVTEQDSKD  STYSLSNTLT  LSKADYEKHK  VYACEVTHQG

201  LSSPVTKSFN  RGEC(SEQ ID NO: 19)
```

(SEQ ID NO: 19)

EXAMPLE 10

Identification of the Epitope for 4A5-3.1.1-B4

The epitope to which 4A5-3.1.1-B4 bound and neutralized human TNFSF13b was determined. Human and murine TNFSF13b sequences were aligned as shown below:

A homology model was created for human TNFSF13b based on the known crystal structure for several TNF family members. Exposed residues that are different between mouse and human TNFSF13b are potential binding sites for 4A5-3.1.1-B4 since 4A5-3.1.1-B4 neutralizes human but not mouse TNFSF13b.

Three potential epitopes were identified: 1) K71, T72, Y73, E105; 2) Q26, S29, L139, D140; and 3) L53, K55, E56, K119.

Mutagenesis was performed to make chimeric molecules by changing the amino acid sequence from human to mouse. Chimera A was L139R, D140N; Chimera B was K71P, T72I, Y73F; Chimera C was K71P, T72I, Y73F, E105K; Chimera D was L53V, K55R, E56Q; Chimera E was E105K.

Using the proliferation assay as described in Example 2, all of the chimeras were tested for functional activity and neutralization by 4A5-3.1.1-B4. Initial assays were performed

```
Mouse TNFSF13b    1 AFQGPEETEQ DVDLSAPPAP CLPGCRHSQH DDNGMNLRNI IQDCLQLIA   49
Human TNFSF13b    1 AVQGPEE--- ---------- ---------- --------TV TQDCLQLIA   18

Mouse TNFSF13b   50 DSDTPTIRKG TYTFVPWLLS FKRGNALEEK ENKIVVRQTG YFFIYSQVLY   99
Human TNFSF13b   19 DSETPTIQKG SYTFVPWLLS FKRGSALEEK ENKILVKETG YFFIYGQVLY   68

Mouse TNFSF13b  100 TDPIFAMGHV IQRKKVHVFG DELSLVTLFR CIQNMPKTLP NNSCYSAGIA  149
Human TNFSF13   69 TDKTYAMGHL IQRKKVHVFG DELSLVTLFR CIQNMPETLP NNSCYSAGIA  118

Mouse TNFSF13b  150 RLEEGDEIQL AIPRENAQIS RNGDDTFFGA LKLL                  183
                       SEQ ID NO: 22.
Human TNFSF13b  119 KLEEGDELQL AIPRENAQIS LDGDVTFFGA LKLL                  152
                       SEQ ID NO: 21."
``` using supernatants from 293 transient transfections for each of the chimeras and both human TNFSF13b and murine TNFSF13b parent molecules. All of the chimeras induced similar proliferation indicating that the chimeras produced were functional. Using 6 ug/ml of 4A5-3.1.1-B4, 100% neutralization was observed with human TNFSF13b and chimeras A, B, D and E. No neutralization was observed for murine TNFSF13b or chimera C. Purified TNFSF13b mutants were produced for chimera A, B, and C and the assay was repeated using 11 ng/ml of each parent TNFSF13b or chimera TNFSF13b and 1 ug/ml of 4A5-3.1.1-B4. The results showed 100% neutralization was observed with human TNFSF13b and chimera A, 88% neutralization with chimera B, and no neutralization was observed for murine TNFSF13b or chimera C.

EXAMPLE 11

In Vivo Studies Using 4A5-3.1.1-B4

Transgenic mice overexpressing soluble human TNFSF13b are generated using established techniques as described by Hogan, B. et al. (1986) *Manipulating the Mouse Embryo: A Laboratory Manual*. Cold Spring Harbor Laboratory, NY] as modified by Fox and Solter (*Mol. Cell. Biol.* 8: 5470, 1988). Briefly, a DNA fragment encompassing the hTNFSF13b gene is microinjected into the male pronuclei of newly fertilized one-cell-stage embryos (zygotes) of the FVB/N strain. The embryos are cultured in vitro overnight to allow development to the two-cell-stage. Two-cell embryos are then transplanted into the oviducts of pseudopregnant CD-1 strain mice to allow development to term. To test for the presence of the transgene in the newborn mice, a small piece of toe is removed from each animal and digested with proteinase K to release the nucleic acids. A sample of the toe extract is subsequently subjected to PCR analysis to identify transgene-containing mice.

The hTNFSF13b transgenic mice had a dramatic increase in peripheral B cells, generally about three fold compared to age and sex matched littermates. There was a slight increase in peripheral T cells as well. The hTNFSF13b transgenic mice were treated with 4A5-3.1.1-B4 to determine if neutralization of hTNFSF13b would result in a reduction in B cell numbers back to normal levels. At 15 weeks old, female hTNFSF13b mice were injected subcutaneously twice a week for three weeks with either 25 ug of 4A5-3.1.1-B4 or isotype control antibody. Four days after the last injection of antibody, the mice were sacrificed and the spleen removed for analysis. B and T cell numbers were calculated by determining the percentage of CD19+ cells, for B cells, and CD3+ cells, for T cells using flow cytometry and absolute white blood cell count for each spleen. The results are shown below demonstrate that in vivo administration of 4A5-3.1.1-B4 to hTNFSF13b transgenic mice is able to restore the normal numbers of T and B cells (average±standard deviation)

| Treatment Group | B cells ($\times 10^6$) | T cells ($\times 10^6$) |
|---|---|---|
| Wild type littermates | 29 ± 11 | 46 ± 15 |
| Transgenic + Isotype mAb | 122 ± 30 | 75 ± 14 |
| Transgenic + 4A5 mAb | 29 ± 5 | 46 ± 12 |

SEQUENCE LISTING

```
<160> NUMBER OF SEQ ID NOS: 26

<210> SEQ ID NO 1
<211> LENGTH: 327
<212> TYPE: DNA
<213> ORGANISM: Homo sapiens

<400> SEQUENCE: 1
gaaattgtgt tgacgcagtc tccagccacc ctgtctttgt ctccagggga aagagccacc      60
ctctcctgca gggccagtca gagtgttagc cgctacttag cctggtacca gcagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctcggac gttcggccaa     300
gggaccaagg tggaaatcaa acgaact                                         327

<210> SEQ ID NO 2
<211> LENGTH: 109
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30
```

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr
            100                 105

<210> SEQ ID NO 3
<211> LENGTH: 33
<212> TYPE: DNA
<213> ORGANISM: Homo sapiens

<400> SEQUENCE: 3
agggccagtc agagtgttag ccgctactta gcc                                    33

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Arg Tyr Leu Ala
1               5                   10

<210> SEQ ID NO 5
<211> LENGTH: 21
<212> TYPE: DNA
<213> ORGANISM: Homo sapiens

<400> SEQUENCE: 5
gatgcatcca acagggccac t                                                 21

<210> SEQ ID NO 6
<211> LENGTH: 7
<212> TYPE: PRT
<213> ORGANISM: Homo sapiens

<400> SEQUENCE: 6

Asp Ala Ser Asn Arg Ala Thr
1               5

<210> SEQ ID NO 7
<211> LENGTH: 27
<212> TYPE: DNA
<213> ORGANISM: Homo sapiens

<400> SEQUENCE: 7
cagcagcgta gcaactggcc tcggacg                                           27

<210> SEQ ID NO 8
<211> LENGTH: 9
<212> TYPE: PRT
<213> ORGANISM: Homo sapiens

<400> SEQUENCE: 8

Gln Gln Arg Ser Asn Trp Pro Arg Thr
1               5
```

```
<210> SEQ ID NO 9
<211> LENGTH: 426
<212> TYPE: DNA
<213> ORGANISM: Homo sapiens
<220> FEATURE:
<221> NAME/KEY: sig_peptide
<222> LOCATION: (1)..(57)

<400> SEQUENCE: 9
atgaaacacc tgtggttctt cctcctcctg gtggcagctc ccagatgggt cctgtcccag      60
gtgcaactac agcagtgggg cgcaggactg ttgaagcctt cggagaccct gtccctcacc     120
tgcgctgtct atggtgggtc cttcagtggt tactactgga gctggatccg ccagcccca     180 gggaagggc tggagtggat tgggaaatc aatcatagtg aagcaccaa ctacaacccg       240 tccctcaaga gtcgagtcac catatcagta gacacgtcca agaaccagtt ctccctgaaa     300
ctgagctctg tgaccgccgc ggacacggct gtgtattact gtgcgagagg gtattacgat     360
attttgactg gttattatta ctactttgac tactggggcc agggaaccct ggtcaccgtc     420
tcctca                                                                426

<210> SEQ ID NO 10
<211> LENGTH: 142
<212> TYPE: PRT
<213> ORGANISM: Homo sapiens
<220> FEATURE:
<221> NAME/KEY: SIGNAL
<222> LOCATION: (1)..(19)

<400> SEQUENCE: 10

Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Pro Pro Gly Lys Gly Leu
    50                  55                  60

Glu Trp Ile Gly Glu Ile Asn His Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Gly Tyr Tyr Asp Ile Leu Thr Gly Tyr Tyr Tyr Tyr
        115                 120                 125

Phe Asp Tyr Trp Gly Gln Gly Thr Leu Val Thr Val Ser Ser
    130                 135                 140

<210> SEQ ID NO 11
<211> LENGTH: 15
<212> TYPE: DNA
<213> ORGANISM: Homo sapiens

<400> SEQUENCE: 11
ggttactact ggagc                                                       15

<210> SEQ ID NO 12
<211> LENGTH: 5
<212> TYPE: PRT
<213> ORGANISM: Homo sapiens
```

```
<400> SEQUENCE: 12

Gly Tyr Tyr Trp Ser
1               5

<210> SEQ ID NO 13
<211> LENGTH: 48
<212> TYPE: DNA
<213> ORGANISM: Homo sapiens

<400> SEQUENCE: 13
gaaatcaatc atagtggaag caccaactac aacccgtccc tcaagagt          48

<210> SEQ ID NO 14
<211> LENGTH: 16
<212> TYPE: PRT
<213> ORGANISM: Homo sapiens

<400> SEQUENCE: 14

Glu Ile Asn His Ser Gly Ser Thr Asn Tyr Asn Pro Ser Leu Lys Ser
1               5                   10                  15

<210> SEQ ID NO 15
<211> LENGTH: 45
<212> TYPE: DNA
<213> ORGANISM: Homo sapiens

<400> SEQUENCE: 15
gggtattacg atattttgac tggttattat tactactttg actac             45

<210> SEQ ID NO 16
<211> LENGTH: 15
<212> TYPE: PRT
<213> ORGANISM: Homo sapiens

<400> SEQUENCE: 16

Gly Tyr Tyr Asp Ile Leu Thr Gly Tyr Tyr Tyr Tyr Phe Asp Tyr
1               5                   10                  15

<210> SEQ ID NO 17
<211> LENGTH: 450
<212> TYPE: PRT
<213> ORGANISM: Homo sapiens

<400> SEQUENCE: 17

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ile Leu Thr Gly Tyr Tyr Tyr Tyr Phe Asp Tyr
            100                 105                 110

Trp Gly Gln Gly Thr Leu Val Thr Val Ser Ser Ala Ser Thr Lys Gly
        115                 120                 125
```

```
Pro Ser Val Phe Pro Leu Ala Pro Cys Ser Arg Ser Thr Ser Glu Ser
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Gln Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 18
<211> LENGTH: 453
<212> TYPE: PRT
<213> ORGANISM: Homo sapiens

<400> SEQUENCE: 18

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
```

-continued

```
                35                  40                  45
Gly Glu Ile Asn His Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Tyr Tyr Asp Ile Leu Thr Gly Tyr Tyr Tyr Phe Asp Tyr
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 19
<211> LENGTH: 214
<212> TYPE: PRT
<213> ORGANISM: Homo sapiens

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Asn Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 15
<212> TYPE: PRT
<213> ORGANISM: Homo sapiens

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 152
<212> TYPE: PRT
<213> ORGANISM: Homo sapiens

<400> SEQUENCE: 21

Ala Val Gln Gly Pro Glu Glu Thr Val Thr Gln Asp Cys Leu Gln Leu
1               5                   10                  15

Ile Ala Asp Ser Glu Thr Pro Thr Ile Gln Lys Gly Ser Tyr Thr Phe
            20                  25                  30

Val Pro Trp Leu Leu Ser Phe Lys Arg Gly Ser Ala Leu Glu Glu Lys
        35                  40                  45

```
Glu Asn Lys Ile Leu Val Lys Glu Thr Gly Tyr Phe Phe Ile Tyr Gly
                50                  55                  60
Gln Val Leu Tyr Thr Asp Lys Thr Tyr Ala Met Gly His Leu Ile Gln
65                  70                  75                  80
Arg Lys Lys Val His Val Phe Gly Asp Glu Leu Ser Leu Val Thr Leu
                    85                  90                  95
Phe Arg Cys Ile Gln Asn Met Pro Glu Thr Leu Pro Asn Asn Ser Cys
                100                 105                 110
Tyr Ser Ala Gly Ile Ala Lys Leu Glu Glu Gly Asp Glu Leu Gln Leu
                115                 120                 125
Ala Ile Pro Arg Glu Asn Ala Gln Ile Ser Leu Asp Gly Asp Val Thr
130                 135                 140
Phe Phe Gly Ala Leu Lys Leu Leu
145                 150
```

<210> SEQ ID NO 22
<211> LENGTH: 183
<212> TYPE: PRT
<213> ORGANISM: Mus musculus

<400> SEQUENCE: 22

```
Ala Phe Gln Gly Pro Glu Glu Thr Glu Gln Asp Val Asp Leu Ser Ala
1               5                   10                  15
Pro Pro Ala Pro Cys Leu Pro Gly Cys Arg His Ser Gln His Asp Asp
            20                  25                  30
Asn Gly Met Asn Leu Arg Asn Ile Ile Gln Asp Cys Leu Gln Leu Ile
        35                  40                  45
Ala Asp Ser Asp Thr Pro Thr Ile Arg Lys Gly Thr Tyr Thr Phe Val
50                  55                  60
Pro Trp Leu Leu Ser Phe Lys Arg Gly Asn Ala Leu Glu Glu Lys Glu
65                  70                  75                  80
Asn Lys Ile Val Val Arg Gln Thr Gly Tyr Phe Phe Ile Tyr Ser Gln
                85                  90                  95
Val Leu Tyr Thr Asp Pro Ile Phe Ala Met Gly His Val Ile Gln Arg
                100                 105                 110
Lys Lys Val His Val Phe Gly Asp Glu Leu Ser Leu Val Thr Leu Phe
            115                 120                 125
Arg Cys Ile Gln Asn Met Pro Lys Thr Leu Pro Asn Asn Ser Cys Tyr
130                 135                 140
Ser Ala Gly Ile Ala Arg Leu Glu Glu Gly Asp Glu Ile Gln Leu Ala
145                 150                 155                 160
Ile Pro Arg Glu Asn Ala Gln Ile Ser Arg Asn Gly Asp Asp Thr Phe
                165                 170                 175
Phe Gly Ala Leu Lys Leu Leu
            180
```

<210> SEQ ID NO 23
<211> LENGTH: 119
<212> TYPE: PRT
<213> ORGANISM: Homo sapiens

<400> SEQUENCE: 23

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Arg Tyr
            20                  25                  30
```

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
     50                  55                  60

Ser Gly Ser Gly Thr Asp Ser Thr Leu Thr Ile Ser Ser Leu Glu Pro
 65                  70                  75                  80

Glu Asp Phe Ala Val Tyr Tyr Cys Gln Gln Arg Ser Asn Trp Pro Arg
                 85                  90                  95

Thr Phe Gly Gln Gly Thr Lys Val Glu Ile Lys Arg Thr Val Ala Ala
            100                 105                 110

Pro Ser Val Phe Ile Phe Pro
            115

<210> SEQ ID NO 24
<211> LENGTH: 357
<212> TYPE: DNA
<213> ORGANISM: Homo sapiens

<400> SEQUENCE: 24
gaaattgtgt tgacgcagtc tccagccacc ctgtctttgt ctccagggga aagagccacc      60
ctctcctgca gggccagtca gagtgttagc cgctacttag cctggtacca gcagaaacct     120
ggccaggctc ccaggctcct catctatgat gcatccaaca gggccactgg catcccagcc     180
aggttcagtg gcagtgggtc tgggacagac tccactctca ccatcagcag cctagagcct     240
gaagattttg cagtttatta ctgtcagcag cgtagcaact ggcctcggac gttcggccaa     300
gggaccaagg tggaaatcaa acgaactgtg gctgcaccat ctgtcttcat cttcccg        357

<210> SEQ ID NO 25
<211> LENGTH: 154
<212> TYPE: PRT
<213> ORGANISM: Homo sapiens

<400> SEQUENCE: 25

Met Lys His Leu Trp Phe Phe Leu Leu Leu Val Ala Ala Pro Arg Trp
 1               5                  10                  15

Val Leu Ser Gln Val Gln Leu Gln Gln Trp Gly Ala Gly Leu Leu Lys
             20                  25                  30

Pro Ser Glu Thr Leu Ser Leu Thr Cys Ala Val Tyr Gly Gly Ser Phe
            35                  40                  45

Ser Gly Tyr Tyr Trp Ser Trp Ile Arg Gln Pro Pro Gly Lys Gly Leu
 50                  55                  60

Glu Trp Ile Gly Glu Ile Asn His Ser Gly Ser Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Leu Lys Leu Ser Ser Val Thr Ala Ala Asp Thr Ala Val Tyr
            100                 105                 110

Tyr Cys Ala Arg Gly Tyr Tyr Asp Ile Leu Thr Gly Tyr Tyr Tyr Tyr
            115                 120                 125

Phe Asp Tyr Trp Gly Gln Gly Thr Leu Val Thr Val Ser Ser Ala Ser
        130                 135                 140

Thr Lys Gly Pro Ser Val Phe Pro Leu Ala
145                 150

<210> SEQ ID NO 26
<211> LENGTH: 462

-continued

```
<212> TYPE: DNA
<213> ORGANISM: Homo sapiens

<400> SEQUENCE: 26
atgaaacacc tgtggttctt cctcctcctg gtggcagctc ccagatgggt cctgtcccag        60
gtgcaactac agcagtgggg cgcaggactg ttgaagcctt cggagaccct gtccctcacc       120
tgcgctgtct atggtgggtc cttcagtggt tactactgga gctggatccg ccagccccca       180 gggaagggc tggagtggat tggggaaatc aatcatagtg gaagcaccaa ctacaacccg        240
tccctcaaga gtcgagtcac catatcagta gacacgtcca agaaccagtt ctccctgaaa       300
ctgagctctg tgaccgccgc ggacacggct gtgtattact gtgcgagagg gtattacgat       360
attttgactg gttattatta ctactttgac tactggggcc agggaaccct ggtcaccgtc       420
tcctcagcct ccaccaaggg cccatcggtc ttccccctgg ca                         462
```

I claim:

1. A pharmaceutical composition comprising an anti-hTNFSF13b human antibody, Fab fragment, Fab' fragment, F(ab')2 fragment, or single chain FV fragment which comprises SEQ ID NO: 2 and SEQ ID NO: 10.

2. A pharmaceutical composition comprising an anti-hTNFSF13b human antibody which comprises SEQ ID NO: 17 and SEQ ID NO: 19.

3. A pharmaceutical composition comprising an anti-hTNFSF13b human antibody which comprises SEQ ID NO: 18 and SEQ ID NO: 19.

* * * * *

UNITED STATES PATENT AND TRADEMARK OFFICE
CERTIFICATE OF CORRECTION

PATENT NO. : 7,728,109 B2  
APPLICATION NO. : 11/952363  
DATED : June 1, 2010  
INVENTOR(S) : Kikly Page 1 of 6

It is certified that error appears in the above-identified patent and that said Letters Patent is hereby corrected as shown below:

In the issued patent, please delete the sequence listing col. 28 below:

<210> 11  
    <211> 15  
    <212> DNA  
    <213> Homo sapiens

<400> 11  
" ggttactact ggagc          "

And insert:

<210> 11  
    <211> 30  
    <212> DNA  
    <213> Homo sapiens

<400> 11  
-- ggtgggtcct tcagtggtta ctactggagc --

In the issued patent, please delete the sequence listing below:

<210> 12  
    <211> 5  
    <212> PRT  
    <213> Homo sapiens

<400> 12

Gly Tyr Tyr Trp Ser  
"  1                 5    "

And insert:

<210> 12  
--
<211> 10

Signed and Sealed this  
Twenty-eighth Day of June, 2011

David J. Kappos  
*Director of the United States Patent and Trademark Office*

<212> PRT
<213> Homo sapiens

<400> 12

Gly Gly Ser Phe Ser Gly Tyr Tyr Trp Ser
1                5                    10 --

In the sequence listing, please delete:

<210> 16
<211> 15
<212> PRT
<213> Homo sapiens

<400> 16

" Gly Tyr Tyr Asp Ile Leu Thr Gly Thr Thr Thr Thr Phe Asp Tyr
  1               5                  10                 15 "

And insert:

<210> 16
<211> 15
<212> PRT
<213> Homo sapiens

<400> 16

-- Gly Tyr Tyr Asp Ile Leu Thr Gly Tyr Tyr Tyr Tyr Phe Asp Tyr
   1               5                  10                 15 --

In the sequence listing, please delete:

<210> 17
<211> 450
<212> PRT
<213> Homo sapiens

<400> 17

Gln Val Gln Leu Gln Gln Trp Gly Ala Gly Leu Leu Lys Pro Ser Glu
1               5                  10                  15

Thr Leu Ser Leu Thr Cys Ala Val Tyr Gly Gly Ser Phe Ser Gly Tyr
           20                  25                  30

Tyr Trp Ser Trp Ile Arg Gln Pro Pro Gly Lys Gly Leu Glu Trp Ile
           35                  40                  45

" Gly Glu Ile Asn His Ser Gly Ser Thr Asn Tyr Asn Pro Ser Leu Lys

```
                 50                  55                  60

Ser Arg Val Thr Ile Ser Val Asp Thr Ser Lys Asn Gln Phe Ser Leu
         65                  70                  75                  80

Lys Leu Ser Ser Val Thr Ala Ala Asp Thr Ala Val Tyr Tyr Cys Ala
                             85                  90                  95

Arg Gly Tyr Tyr Asp Ile Leu Thr Gly Tyr Tyr Tyr Phe Asp Tyr
                            100                 105                 110

Trp Gly Gln Gly Thr Leu Val Thr Val Ser Ser Ala Ser Thr Lys Gly
                            115                 120                 125

Pro Ser Val Phe Pro Leu Ala Pro Cys Ser Arg Ser Thr Ser Glu Ser
                 130                 135                 140

Thr Ala Ala Leu Gly Cys Leu Val Lys Asp Tyr Phe Pro Glu Pro Val
         145                 150                 155                 160

Thr Val Ser Trp Asn Ser Gly Ala Leu Thr Ser Gly Val His Thr Phe
                            165                 170                 175

Pro Ala Val Leu Gln Ser Ser Gly Leu Tyr Ser Leu Ser Ser Val Val
                            180                 185                 190

Thr Val Pro Ser Ser Ser Leu Gly Thr Lys Thr Tyr Thr Cys Asn Val
                            195                 200                 205

Asp His Lys Pro Ser Gln Thr Lys Val Asp Lys Arg Val Glu Ser Lys
                            210                 215                 220

Tyr Gly Pro Pro Cys Pro Pro Cys Pro Ala Pro Glu Phe Leu Gly Gly
         225                 230                 235                 240

Pro Ser Val Phe Leu Phe Pro Pro Lys Pro Lys Asp Thr Leu Met Ile
                            245                 250                 255

Ser Arg Thr Pro Glu Val Thr Cys Val Val Val Asp Val Ser Gln Glu
                            260                 265                 270

Asp Pro Glu Val Gln Phe Asn Trp Tyr Val Asp Gly Val Glu Val His
```

CERTIFICATE OF CORRECTION (continued)
U.S. Pat. No. 7,728,109 B2

```
                275             280             285

Asn Ala Lys Thr Lys Pro Arg Glu Glu Gln Phe Asn Ser Thr Tyr Arg
        290             295             300

Val Val Ser Val Leu Thr Val Leu His Gln Asp Trp Leu Asn Gly Lys
    305             310             315             320

Glu Tyr Lys Cys Lys Val Ser Asn Lys Gly Leu Pro Ser Ser Ile Glu
                325             330             335

Lys Thr Ile Ser Lys Ala Lys Gly Gln Pro Arg Glu Pro Gln Val Tyr
            340             345             350

Thr Leu Pro Pro Ser Gln Glu Glu Met Thr Lys Asn Gln Val Ser Leu
        355             360             365

Thr Cys Leu Val Lys Gly Phe Tyr Pro Ser Asp Ile Ala Val Glu Trp
        370             375             380

Glu Ser Asn Gly Gln Pro Glu Asn Asn Tyr Lys Thr Thr Pro Pro Val
    385             390             395             400

Leu Asp Ser Asp Gly Ser Phe Phe Leu Tyr Ser Arg Leu Thr Val Asp
                405             410             415

Lys Ser Arg Trp Gln Glu Gly Asn Val Phe Ser Cys Ser Val Met His
            420             425             430

Glu Ala Leu His Asn His Tyr Thr Gln Lys Ser Leu Ser Leu Ser Leu
            435             440             445

Gly Lys
    450
```
"

And insert:

<210> 17
<211> 450
<212> PRT
<213> Homo sapiens

--
<400> 17

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65              70                  75                      80

Lys Leu Ser Ser Val Thr Ala Ala Asp Thr Ala Val Tyr Tyr Cys Ala
                85                  90                  95

Arg Gly Tyr Tyr Asp Ile Leu Thr Gly Tyr Tyr Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450 --